United States Patent [19]

Fong

[11] Patent Number: 6,008,338
[45] Date of Patent: Dec. 28, 1999

[54] ALL-TRANS RETINALDEHYDE BINDING PROTEIN, DNA ENCODING SAME, AND ANTIBODIES THERETO

[76] Inventor: Henry K.W. Fong, 1850 E. Calaveras St., Altadena, Calif. 91001

[21] Appl. No.: 09/090,947

[22] Filed: Jun. 5, 1998

Related U.S. Application Data

[62] Division of application No. 08/358,171, Dec. 16, 1994, Pat. No. 5,763,578.
[51] Int. Cl.⁶ .......................... C07N 21/06; C12N 15/12; C12N 15/13
[52] U.S. Cl. .......................... 536/23.5; 536/29.3; 435/6; 435/320.1; 435/325; 435/253.3; 435/69.1; 530/300; 530/350
[58] Field of Search .................. 536/23.5, 24.3; 435/6, 320.1, 325, 252.3, 64.1; 530/350, 300

[56] References Cited

U.S. PATENT DOCUMENTS 5,527,677  6/1996  Deguchi et al. ............................. 435/6
5,575,939  11/1996  Bavik et al. .
5,849,501  12/1998  Lin et al. ................................. 435/7.1

FOREIGN PATENT DOCUMENTS

94/09081  4/1994  WIPO .

OTHER PUBLICATIONS

Bernstein et al, "Assay of the Retinoid Isomerase System of the Eye", *Methods in Enzymology* 189:494–503 (1990).

Crabb et al, "The Complete Primary Structure of the Cellular Retinaldehyde–binding Protein from Bovine Retina", *J. Biol. Chem.* 263(35):18678–18687 (1988).

Crabb et al, "Cloning of the cDNAs Encoding the Cellular Retinaldehyde–binding Protein from Bovine and Human Retina and Comparison of the Protein Structures", *J. Biol. Chem.* 263(35):18688–18692 (1988).

Donoso et al, "Retinal Pigment Epithelial Cell Plasma Membrane: A Monoclonal Antibody Study", *Hybridoma* 7(3):265–272 (1988).

Fong et al, "Molecular Cloning of a Novel G Protein Coupled Receptor, Most Closely Resembling the Visual Pigment Family, from Bovine Retinal Pigment Epithelium and Inner Retina", IOUS, vol. 34, Mar. 15, 1993.

Hara et al, "New Photosensitive Pigment Found in the Retina of the Squid Ommastrephes", *Nature* 206:1331–1334 (1965).

Hara–Nishimura et al, "Cloning and nucleotide sequence of cDNA for retinochrome, retinal photoisomerase from squid retina", *FEBS Letters* 271(1,2):106–110 (1990).

Jiang et al, "Differential Hybridization and Molecular Cloning of Selective Expressed RPE Messenger RNA", IOUS, vol. 33, Mar. 15, 1993.

Levin et al, "Structure–Function Analyses of Mammalian Cellular Retinol–Binding Proteins by Expression in *Escherichia coli*", *Methods in Enzymology* 189:506–520 (1990).

Livrea et al, "Assay of all–trans 11–cis–Retinoid Isomerase Activity in Bovine Retinal Pigment Epithelium" *Methods in Enzymology* 189:503–506 (1990).

Matthews et al, "Tautomeric Forms of Metarhodopsin" *J. Gen. Physiology* 47:215–240 (1963).

(List continued on next page.)

*Primary Examiner*—Elizabeth Kemmerer
*Assistant Examiner*—Nirmaz S. Basi
*Attorney, Agent, or Firm*—Browdy and Neimark

[57] ABSTRACT

An isolated DNA molecule encodes a photoreceptive retinaldehyde-binding protein of the visual system and brain. The isolated protein is a putative receptor for an all-trans-retinylidene chromophore that absorbs light in the visible range. Antibodies are disclosed which specifically bind to such retinaldehyde binding protein. An altered retinaldehyde binding protein with a 38 amino acid deletion is an indicator of abnormality in the retinal pigment epithelium. Antibodies are also disclosed which are specific to the altered retinaldehyde binding protein.

16 Claims, 10 Drawing Sheets

OTHER PUBLICATIONS

Nathans et al, "Isolation, Sequence Analysis, and Intron--Exon Arrangement of the Gene Encoding Bovine Rhodopsin", *Cell* 34:807–814 (1963).

Nathans et al, "Molecular Genetics of Human Color Vision: The Genes Encoding Blue, Green, and Red Pigments", *Science* 232:193–202 (1986).

Pandey et al, "Immunohistochemical Localization of a Novel G Protein Coupled Receptor Preferentially Expressed in RPE and Retina", IOUS, vol. 34, Mar. 15, 1993.

Sakmar et al, "Glutamic acid–113 serves as theretinylidene Schiff base counterion in bovine rhodopsin", *Proc. Natl. Acad. Sci. USA* 86:8309–9313 (1989).

Zhou et al, "Generation and Characterization of Antibodies to Adhesion–related Molecules of Retinal Pigment Epithelial Cells", *Exp. Eye Res.* 58:585–594 (1994).

Sigma Chemical Co. Catalog, p. 1493 (1990).

Wallace, B et al. Methods in Enzymology, vol. 152, pp. 432–443, May 1987.

Shen et al., A Human Opsin–Related Gene That Encodes a Retinaldehyde–Binding Protein. Biochemistry, vol. 33, pp. 13117–13125, 1994.

Jiang, M. et al., An Opsin Homologue in the Retina and Pigment Epithelium. Ophthalmology and Visual Science, vol. 34. No. 13, pp. 3669–3678, 1993.

Suggs, V. S. et al, PNAS, USA, vol. 78, No. 11, pp. 6613–6617, 1981.

```
   1    GAGAAAGGCAGAGAGAATGGCAGAGTCTGGGACCCTGCCCACTGGCTTCGGGGAGCTG
   1                     MetAlaGluSerGlyThrLeuProThrGlyPheGlyGluLeu

59    GAGGTGCTGGCCGTGGGGACGGTGCTGCTGGTGGAAGCTCTTTCTGGTCTCAGCCTAAAC
  15    GluValLeuAlaValGlyThrValLeuLeuValGluAlaLeuSerGlyLeuSerLeuAsn

119    ATCCTGACCATCCTCTCTTTCTGCAAGACCCCAGAGCTGCGGACCCCCAGCCACCTGCTG
  35    IleLeuThrIleLeuSerPheCysLysThrProGluLeuArgThrProSerHisLeuLeu

179    GTGTTGAGCTTGGCGCTGGCCGACAGTGGAATCAGCCTGAACGCCCTCGTTGCAGCCACG
  55    ValLeuSerLeuAlaLeuAlaAspSerGlyIleSerLeuAsnAlaLeuValAlaAlaThr

239    TCCAGCCTCCTCCGGCGCTGGCCCTACGGCTCGGAAGGCTGCCAGGCTCACGGCTTCCAG
  75    SerSerLeuLeuArgArgTrpProTyrGlySerGluGlyCysGlnAlaHisGlyPheGln

299    GGCTTTGTCACGGCACTGGCCAGCATCTGCAGCAGCGCAGCCGTCGCCTGGGGCGCTAT
  95    GlyPheValThrAlaLeuAlaSerIleCysSerSerAlaAlaValAlaTrpGlyArgTyr

359    CACCACTTCTGCACCCGCAGCCGACTGGATTGGAACACGGCCGTCTCCCTGGTGTTCTTC
 115    HisHisPheCysThrArgSerArgLeuAspTrpAsnThrAlaValSerLeuValPhePhe

419    GTATGGCTGTCTTCTGCCTTCTGGGCAGCACTGCCCCTCCTGGGCTGGGGCCACTATGAC
 135    ValTrpLeuSerSerAlaPheTrpAlaAlaLeuProLeuLeuGlyTrpGlyHisTyrAsp

479    TATGAGCCGCTGGGGACCTGCTGCACTCTGGACTATTCCAGGGGGGACAGAAACTTCACC
 155    TyrGluProLeuGlyThrCysCysThrLeuAspTyrSerArgGlyAspArgAsnPheThr

539    AGCTTCCTTTTCACCATGGCCTTTTTCAACTTCCTCCTGCCCCTCTTCATCACAGTCGTG
 175    SerPheLeuPheThrMetAlaPhePheAsnPheLeuLeuProLeuPheIleThrValVal

599    TCCTATCGGCTCATGGAGCAGAAACTCGGGAAGACCAGCCGTCCCCCGGTGAACACCGTC
 195    SerTyrArgLeuMetGluGlnLysLeuGlyLysThrSerArgProProValAsnThrVal

659    CTGCCAGCCAGGACGCTGCTGCTCGGCTGGGGCCCCTACGCTCTCCTGTATCTGTATGCC
 215    LeuProAlaArgThrLeuLeuLeuGlyTrpGlyProTyrAlaLeuLeuTyrLeuTyrAla

719    ACCATCGCGGATGCAACCTCCATCTCCCCCAAGCTGCAGATGGTGCCCGCTCTCATTGCC
 235    ThrIleAlaAspAlaThrSerIleSerProLysLeuGlnMetValProAlaLeuIleAla

779    AAGGCAGTACCCACAGTCAACGCCATGAACTATGCCCTGGGCAGCGAGATGGTGCACAGG
 255    LysAlaValProThrValAsnAlaMetAsnTyrAlaLeuGlySerGluMetValHisArg

839    GGAATCTGGCAATGCCTCTCGCCACAGAGGAGAGAGCACAGCCGAGAGCAGTGAGCCTCT
 275    GlyIleTrpGlnCysLeuSerProGlnArgArgGluHisSerArgGluGln *

899    CTGGGGGGCTTCCCAGACCCAGGCCCACCCTGGCCTTCCTGGACTGAGCCCCTGCCTGGG
 959    GAATCCTGTCCAGCAGCCTCAGGAGCCAAGCTCCAAACACTCACCCTTCATCCCCGATGG
1019    CCCTTTGAGCCTGGTCCAAGGCTGGACACAGGGGATTCAGAGAAAACCAGACTACATGG
1079    AATGAGCCCGGACTCTGGAGCCACACGGACCTGTGTTGGCCATAGCTCTCCACATAGAGG
1139    CTGAGAGACCTTGGAAAAGTCACACTCTCTGACTCTGCTTCCTGGCCCCTAACGTAAGGA
1199    TGTTAATACGGACTTTGGGTCTGTAGTGAAGCTTGAACTTGGTAGCATATATTCATATAC
1259    ACATAGAAGCTGCTGCTCATTAGTACAGCTCTTAGGATTCAGAGACCTACATAGAAGGG
1319    TGAGAGCCCCAGGTCTGGTTGTGGGAGCTCAGCCCAGGCTGCCAGTGTTCAAACACCTCT
1379    TATTAAATCGTGATCTCGTACAGGTGACTTCCAAAAAAAAAA
```

FIG. 1

MAESGTLPTGFGELEVLAVGTVLLVEALSGLSLNILTILSFCKTPELRTPSHLLVLSLAL 60
                                I
ADSGISLNALVAATSSLLRRWPYGSEGCQAHGFQGFVTALASICSSAAVAWGRYHHFCTR 120
      II                                III
SRLDWNTAVSLVFFVWLSSAFWAALPLLGWGHYDYEPLGTCCTLDYSRGDRNFTSFLFTM 180
         IV
AFFNELLPLFITVVSYRLMEQKLGKTSRPPVNTVLPARTLLLGWGPYALLYLYATIADAT 240
      V                                        VI
SISPKLQMVPALIAKAVPTVNAMNYALGSEMVHRGIWQCLSPQRREHSREQ* 291
       VII
         ▲

FIG. 3

```
  1    AGAGACAGCTGGGCCACTGGCAGTGAGGGAGAGTGAGGATGGCAGAGACCAGTGCCCTG
                                                 M A E T S A L   7
                                                 - - - S G T -
              C                                              ▼
 60    CCCACTGGCTTCGGGGAGCTCGAGGTGCTGGCTGTGGGGATGGTGCTACTGGTGGAAGCT
        P T G F G E L E  V L A V G M V L L V E A              27
        - - - - - - - - - - - - T - - - - - - -
120    CTCTCCGGTCTCAGCCTCAATACCCTGACCATCTTCTCTTTCTGCAAGACCCCGGAGCTG
        L S G L S L N T L T I F S F C  K T P E L               47
        - - - - - - - - I - - - L - - -
180    CGGACTCCCTGCCACCTACTGGTGCTGAGCTTGGCTCTTGCGGACAGTGGGATCAGCCTG
        R T P C H  L L V L S L A L A D S G I S L               67
        - - - S  - - - - - - - - - - - - - - -
240    AATGCCCTCGTTGCAGCCACATCCAGCCTTCTCCGGCGCTGGCCCTACGGCTCGGACGGC
        N A L V A A T S S L L  R R W P Y G S D G               87
        - - - - - - - - - - -  - - - - - - E -
                                                    ←
300    TGCCAGGCTCACGGCTTCCAGGGCTTTGTGACAGCGTTGGCCAGCATCTGCAGCAGTGCA
        C Q A H  G F Q G F V T A L A S I C S S A              107
               ___A290 primer           ▼
360    GCCATCGCATGGGGGCGTTATCACCACTACTGCACCCGTAGCCAGCTGGCCTGGAACTCA
        A I A W G  R Y H H Y C T R S Q L A W N S               127
        - V - - -  - - - - - F - - - R - D - - T
420    GCCGTCTCTCTGGTGCTCTTCGTGTGGCTGTCTTCTGCCTTCTGGGCAGCTCTGCCCCTT
        A V S L V L F V W L S S A F W A A L P L                147   FIG. 5
        - - - - - F - - - - - - - - - - - - - -
480    CTGGGTTGGGGTCACTATGACTATGAGCCACTGGGGACATGCTGCACCCTGGACTACTCC
        L G W G  H Y D Y E P L G T C C T L D Y S               167
        - - - -
540    AAGGGGGACAGAAACTTCACCAGCTTCCTCTTCACCATGTCCTTCTTCAACTTCGCCATG
        K G D R N F T S F L F T M S F F N F A M                187
        R - - - - - - - - - - - A - - - - L L
600    CCCCTCTTCATCACGATCACTTCCTACAGTCTCATGGAGCAGAAACTGGGGAAGAGTGGC
        P L F I T I T S  Y S L M E Q K L G K S G                207
        - - - - - V V - - R - - - - - - - - T S
660    CATCTCCAGGTAAACACCACTCTGCCAGCAAGGACGCTGCTGCTCGGCTGGGGCCCCTAT
        H L Q V N T T L P A R T L L L G W G P Y                227
        R P P - - - V
720    GCCATCCTGTATCTATACGCAGTCATCGCAGACGTGACTTCCATCTCCCCCAAACTGCAG
        A I L Y L Y A V I A  D V T S I S P K L Q               247
        - L - - - - - T - -  - A
780    ATGGTGCCCGCCCTCATTGCCAAAATGGTGCCCACGATCAATGCCATCAACTATGCCCTG
        M V P A L I A K M V P T I N A I N Y A L                267
        - - - - - - - A - - V - - M - - - -
840    GGCAATGAGATGGTCTGCAGGGGAATCTGGCAGTGCCTCTCACCGCAGAAGAGGGAGAAG
        G N E M V C R G I W Q C L S P Q K R E K                287
        - S - - - H - - - - - - - - - R - - H
900    GACCGAACCAAGTGAGCCTGCCACCCTGGAGTGAGCCCCAGGCCAGGAGGCTGTTCCAGG
        D R T K end                                            291
        S - E Q end
                   *
 960   AGTCCTGCCCAGCAGCCTCGGTGGCCAAGCCCAGACACTCACCCACCTTCCCCAGTGGCC
1020   CCGTGGATCCTGGTCCTAGGCTGGACACAGGATTCAGAAAGACACCAGGCTGCACAGAAA
1080   GAGCCAGATGGACCTGAGTGTCGGTCACAGACCCCCTACACTCAAGGCTGAGAGGCCTCAG
1140   GAAAGTCATTCCTTTTTAAAAATAATAATAAATGTAAGGGGGTACAGTGCAGTTTTGTTA
1200   CATGGATAGATTGCCTAGTGGTGAAGTCTGGCGTTTTAGTGTAACCATCACCCTAATAAT
1260   ATACGTTGTACCCATTAAGTTATTTCTCATCCCTCACCCCCTCCCACCCTTGTCACCCTTC
1320   TGAGTCTCCAATGTCTATTATTCCACACTCCATGTCCACGTGTACACATTATTTAGCTCC
1380   CACTTACAAGTGAGAACATGTGGTATTTGACTTTCAAAAAAAAAAAA
```

```
-382 TTTGGAGTATACTCATGTGAGCCTGAGGACACACACACAGGCACCAGGCTTGTTGGGAAC
-322 AGCTGCGGCTCAAATCCCTCCTCCTGCTCCCCTCCCCTGGTTATGCAACTCTTTTCCAAT
-262 TAGGCTCTCAGCCACACACCATTTGGATTCCCCGACCTTAATCCTGTGCAATGGGGCTGA
-202 AATGAATGAGACAGGGCTCCATTCTGGCTTCACAAAGGCTGCATTGTCCAACTCGTGAAT
-142 GGGTTCCTTCTGCTTGGGCCAAGAGGACCATTTGCAGCGGGGAGGCATCCAGAAACAGCC
 -82 CAAGGTCCAACATAATAACCTGCATGTGCCTCCACGCACATGGGATGGCCCTTTAAAAGG
 -22 GAGGGCCTGGCTGTGGGAAGCCᴬGAGACAGCTGGGCCACTGGCAGTGAGGGAGAGTGAGG  38   Exon 1
     ATGGCAGAGACCAGTGCCCTGCCCACTGGCTTCGGGGAGCTCGAGGTGCTGGCTGTGGGG  98
      M  A  E  T  S  A  L  P  T  G  F  G  E  L  E  V  L  A  V  G
     ATGGTGCTACTGGTGGAAGgtgagccaggcagaacctggggtgcagcgggggcccagtgg
      M  V  L  L  V  E
     gttctgaggacccaggccaccagtgtggagctggcaaggagaggagaggtccccaaaccc
     agctgggtgtccggtcccattggctgccttcccctctgtgcccggactcgggggtgttct
     gacaattgaacctgtgaggtgcagcacactgcccgctgggagcagagaggaagccaggca
     agggtcagggagggagggactttgaaaggggacatctgcccaggagatgatcaagagcca
     ggctttaggacttttcatgtccctccagccgggagaaaatttaatccactccttgg....
     .intron 1 (2.2 kb)..gttctgaccccagctgggcctcagcagccccaatgccagc
     ccccacccttcctttcagCTCTCTCCGGTCTCAGCCTCAATACCCTGACCATCTTCTCTT 159 Exon 2
                       A  L  S  G  L  S  L  N  T  L  T  I  F  S
     TCTGCAAGACCCCGGAGCTGCGGACTCCCTGCCACCTACTGGTGCTGAGCTTGGCTCTTG 219
      F  C  K  T  P  E  L  R  T  P  C  H  L  L  V  L  S  L  A  L
     CGGACAGTGGGATCAGCCTGAATGCCCTCGTTGCAGCCACATCCAGCCTTCTCCGgtacc
      A  D  S  G  I  S  L  N  A  L  V  A  A  T  S  S  L  R
     agccccctccccagtccacaggctctggggtcctgcctggggcctgaccctgggccctg
     ggcagccaggccaagggcatttttactacttacagaaaattggccaagg...intron 2
     (1.5 kb)....ggagaggtcactggtgcccagtatctcccacagGCGCTGGCCCTACG   288 Exon 3
                                (V)(S)(H)(R) R  W  P  Y
     GCTCGGACGGCTGCCAGGCTCACGGCTTCCAGGGCTTTGTGACAGCGTTGGCCAGCATCT 348
      G  S  D  G  C  Q  A  H  G  F  Q  G  F  V  T  A  L  A  S  I
     GCAGCAGTGCAGCCATCGCATGGGGGCGTTATCACCACTACTGCACCCgtatgtatctgg
      C  S  S  A  A  I  A  W  G  R  Y  H  H  Y  C  T.
     gctcctggagtggagggacaccgatgcagtgtggagaggataagaggcagggaggggcag
     tcataactagctactgctccgtgtttcccagtacagggaagtgtgggtaggtgtgagtgt
     gcatgcataggcactcatttcagg....intron 3 (4.0 kb)...cacttgaaggga
     cactcttcgagatcaggaagtccattctttctcactctatcaggccatctcctcctcaca
     acctcctcttcttcctctgtcctgtgcagGTAGCCAGCTGGCCTGGAACTCAGCCGTCTC 427 Exon 4
                                   R  S  Q  L  A  W  N  S  A  V  S
     TCTGGTGCTCTTCGTGTGGCTGTCTTCTGCCTTCTGGGCAGCTCTGCCCCTTCTGGGTTG 487
      L  V  L  F  V  W  L  S  S  A  F  W  A  A  L  P  L  L  G  W
     GGGTCACTACGACTATGAGCCACTGGGGACATGCTGCACCCTGGACTACTCCAAGGGGGA 547
      G  H  Y  D  Y  E  P  L  G  T  C  C  T  L  D  Y  S  K  G  D
     CAGgtgaggtgggaggagcagcttcgaggctcctatccatgggaatcttggctttgaact
      R
     cctatgacaagggtgccccagc....intron 4 (4.2 kb)...tgggtccttgaggg
```

FIG. 7A

```
cagctggccatccctgagagctaaccccaatcctccacccgctctccctgtagAAACTTC 557 Exon 5
                                                       N  F
ACCAGCTTCCTCTTCACCATGTCCTTCTTCAACTTCGCCATGCCCCTCTTCATCACGATC 617
 T  S  F  L  F  T  M  S  F  F  N  F  A  M  P  L  F  I  T  I
ACTTCCTACAGTCTCATGGAGCAGAAACTGGGGAAGAGTGGCCATCTCCAGgtaaggacc
 T  S  Y  S  L  M  E  Q  K  L  G  K  S  G  H  L  Q
cccttccggagtgttatctgatggtgcagcgcagctccaggctcttggtgtcccgaacaa
agaattggatgtgacacacacaaacagcaaaacaaatattcattgctttt..intron 5
 (0.5 kb)......aaaaggcttaaggtcacacagtcttaaacaacagagaggcccatct
ggtcccaagttcccctgcagactcagcccctcctgaagcctggtccatgctgccccgcc
ctgctgagtgctgacctggttttcttggccacatagggctgtgggccacctggagcaagc
tgacatctcctgtgacaatttctccccagGTAAACACCACTCTGCCAGCAAGGACGCTGC 699 Exon 6
                               V  N  T  T  L  P  A  R  T  L
TGCTCGGCTGGGGCCCCTATGCCATCCTGTATCTATACGCAGTCATCGCAGACGTGACTT 759
 L  L  G  W  G  P  Y  A  I  L  Y  L  Y  A  V  I  A  D  V  T
CCATCTCCCCCAAACTGCAGATGgtacagatacttctagtacctaaaactagacccctct
 S  I  S  P  K  L  Q  M
ccatctttgttctctgtctcatctcatctcactttctggatttatgacctctgtgtcagt
ctcttcctttct....intron 6 (0.4 kb)...ctttgaagcttcttttctggactt
ttctgccacaacagGTGCCCGCCCTCATTGCCAAAATGGTGCCCACGATCAATGCCATCA 828 Exon 7
               V  P  A  L  I  A  K  M  V  P  T  I  N  A  I
ACTATGCCCTGGGCAATGAGATGGTCTGCAGGGGAATCTGGCAGTGCCTCTCACCGCAGA 888
 N  Y  A  L  G  N  E  M  V  C  R  G  I  W  Q  C  L  S  P  Q
AGAGGGAGAAGGACCGAACCAAGTGAGCCTGCCACCCTGGAGTGAGCCCCAGGCCAGGAG 948
 K  R  E  K  D  R  T  K  *
GCTGTTCCAGGAGTCCTGCCCAGCAGCCTCAGTGGCCAAGCCCAGACACTCACCCACCTT 1008
CCCCAGTGGCCCCGTGGATCCTGGTCCTAGGCTGGACACAGGATTCAGAAAGACACCAGG 1068
CTGCACAGAAAGAGCCAGATGGACCTGAGTGTCGGTCACAGCCCCCTACACTCAAGGCTG 1128
AGAGGCCTCAGGAAAGTCATTCCTTTTTAAAAATAATAATAAATGTAAGGGGGTACAGTG 1188
CAGTTTTGTTACATGGATAGATTGCCTAGTGGTGAAGTCTGGGCTTTTAGTGTAACCATC 1248
ACCCTAATAATATACGTTGTACCCATTAAGTTATTTCTCATCCCTCACCCCCTCCCACCT 1308
TGTCACCCTTCTGAGTCTCCAATGTCTATTATTCCACACTCCATGTCCACGTGTACACAT 1368
TATTTAGCTCCCACTTACAAGTGAGAACATGTGGTATTTGACTTTC/TGTTTTTGAGTTA 1428
TTTCACTTAAA 1439
```

FIG. 7B

ALL-TRANS RETINALDEHYDE BINDING PROTEIN, DNA ENCODING SAME, AND ANTIBODIES THERETO

CROSS-REFERENCE TO RELATED APPLICATIONS

This application is a divisional application of application Ser. No. 08/358,171, filed Dec. 16, 1994, now issued as U.S. Pat. No. 5,763,578, the entire contents of said application is hereby incorporated by reference.

BACKGROUND OF THE INVENTION

1. Field of the Invention

The present invention relates to novel retinaldehyde binding proteins and the DNA encoding them, as well as to conjugate of such binding proteins to retinaldehyde, expression vector and host cells containing such DNA and antibodies to such binding protein.

2. Description of the Background Art

The visual pigments are the light-absorbing proteins in the retina. They have been studied for over 100 years as the centerpiece in the basic process of visual sensory transduction. Each individual pigment consists of a different seven-transmembrane-domain protein, called an opsin, that is bound to a chromophore, 11-cis-retinal (also known as 11-cis-retinaldehyde), via a Schiff base covalent bond. The 11-cis isomer is the chromophore of the majority of naturally occurring opsins. Exposure of opsin-bound retinal to light initiates the cis-trans isomerization and resultant dissociation of retinal from the apoprotein. This catalyzes an enzyme cascade which leads to visual excitation. Humans have four visual pigments, rhodopsin and the red, green, and blue cone pigments, all of which contain 11-cis-retinal as the native chromophore. Each human opsin is found specifically in the retinal photoreceptors, and none are known to be expressed in extraretinal tissue or use all-trans-retinal as a stably bound chromophore. The terms retinal and retinaldehyde are used interchangeably in the art and herein.

The retinal pigment epithelium (RPE) is a specialized cell monolayer that lies adjacent to the photoreceptors that are essential to the visual process. The RPE forms a monolayer of highly differentiated cells that segregates the photoreceptors from the choroidal capillaries. It constitutes part of the blood-retina barrier by regulating the transport of ions, nutrients, and macromolecules between the choroidal blood supply and photoreceptors. It is active in the uptake and storage of retinoids and in the secretion of basement membrane components. The polarized epithelial cells of the RPE are responsible for maintaining the photoreceptors by continually removing the shed fragments of outer segments through phagocytosis. The RPE performs this demanding phagocytic activity to enable each photoreceptor cell to renew its outer segment about every ten days.

The RPE has an important role in the formation of 11-cis-retinal and regeneration of the visual pigments. A lecithin retinol acyl transferase and an isomerohydrolase participate in the endothermic reaction of converting all-trans- to 11-cis-retinoids at the alcohol, rather than aldehyde, oxidation state. The substrate for the isomerohydrolase is an all-trans-retinyl ester, which is converted directly into 11-cis-retinol. The invertebrate visual cycle uses another method to regenerate active visual pigments. In molluscan eyes, there are a pair of photopigment systems, one containing rhodopsin and the other containing retinochrome. Photopigments are regenerated in the rhodopsin-retinochrome conjugate system by exchange of retinal chromophores. Retinochrome binds and photoisomerizes all-trans-retinal to 11-cis-retinal which is returned to the rhodopsin system by the retinal-binding protein, RALBP.

It is believed that aberrations in the functions of the RPE may lead to degeneration of the photoreceptors and to other visual disorders, including age-related macular degeneration (AMD). The molecular basis of RPE atrophy is unknown, and only a few macromolecules are known to be related to diseases of the RPE and retina.

SUMMARY OF THE INVENTION

The present invention is based on the discovery of a novel binding protein, that binds retinaldehyde. The retinaldehyde binding protein of the present invention binds both 11-cis-retinal and all-trans-retinal, and is preferentially expressed in the RPE of the visual system and in the brain. This is the first known vertebrate photoreceptive protein that preferentially binds an all-trans-retinylidene chromophore.

The retinaldehyde binding proteins described herein are preferentially expressed in the RPE, visual system and brain, and their expression reflect normal eye and brain function. A radical change in the structure of these retinaldehyde binding proteins of the invention would be indicative of a molecular aberration in the RPE, visual system or brain. The present invention allows recombinant construction and assay of changes in the retinaldehyde binding proteins of the invention.

One object of the invention is to provide a DNA sequence encoding a retinaldehyde binding protein for use in antisense therapeutics and in the recombinant expression of retinaldehyde binding protein.

Another object of the invention is to provide an altered retinaldehyde binding protein that is indicative of or associated with retinal disease as well as an antibody specific for the altered retinaldehyde binding protein.

A further object of the invention is to provide conjugates of retinaldehyde binding protein with retinaldehyde.

Another object of the invention is to provide antibodies specific to the retinaldehyde binding proteins of the present invention.

Still another object of the invention is to provide an isolated nucleic acid sequence encoding retinaldehyde binding protein.

Yet another object of the invention is to provide an expression vector for expressing the retinaldehyde binding protein.

A still further object of the invention is to provide host cells containing an expression vector for expressing the retinaldehyde binding protein.

It is another object of the invention to provide a method for detecting the altered retinaldehyde binding protein and the corresponding mRNA encoding for the altered retinaldehyde binding protein.

Additional aspects and embodiments of the invention are set forth or readily arise from the drawings described below, or from the following detailed description of the invention.

BRIEF DESCRIPTION OF THE DRAWINGS

FIG. 1 shows nucleotide (SEQ ID NO:1) and deduced amino acid sequence (SEQ ID NO:2) of bovine retinaldehyde binding protein, a putative G protein-coupled receptor. The nucleotide and translated amino acid (three-letter code) sequences were derived from two overlapping cDNA clones, RPE6 and RPE12. The inferred translational initiation codon is the 5'-most ATG triplet, and it begins an open reading frame of 873 nucleotides. The sequences are numbered on the left, using italicized numbering for the amino acid sequence. The polyadenylate tract at the end of the cDNA sequence was about 90 nucleotides long in clone RPE6.

FIG. 3 shows the amino acid sequence of bovine retinaldehyde binding protein (SEQ ID NO:2) and antibody binding sites. The deduced amino acid (one-letter code) sequence of bovine retinaldehyde binding protein was derived from RPE cDNA clones, RPE6 and RPE12. The sequences of the amino and carboxyl terminal peptides used to generate anti-retinaldehyde binding protein antibodies are shown in bold. The positions of the underlined hydrophobic segments I–VII are indicated and are based on analysis according to the Kyte-Doolittle hydrophilicity scale. A lysine residue in the seventh hydrophobic segment, analogous to the retinal attachment site of rhodopsin, is indicated by the triangle. The amino acid sequence is numbered on the right, beginning with the amino-terminal methionine. The amino and carboxyl terminal sequences of bovine retinaldehyde binding protein and rhodopsin are highly divergent.

FIG. 5 shows the nucleotide and deduced amino acid sequence of human retinaldehyde binding protein cDNA. The nucleotide (SEQ ID NO:3) and translated amino acid (one-letter code) (SEQ ID NO:4) sequences for human retinaldehyde binding protein are numbered on the left and right, respectively. Seven stretches of hydrophobic amino acids are shaded. Below the amino acid sequence of human retinaldehyde binding protein is that of the bovine retinaldehyde binding protein (SEQ ID NO:2); for comparison, only amino acid sequence differences are shown and identities are indicated by dashes. The locations of six intervening sequences in the human rgr gene are marked above the cDNA sequence by the inverted triangles. The sequence of the A290 primer (SEQ ID NO:5) is complementary to the cDNA sequence aligned under the arrow. Two sites of nucleotide sequence differences between the cDNA clone HRGR1-2 and human rgr gene clones are indicated by the asterisk. Several amplified copies of the 5'-end cDNA fragment were cloned and sequenced, and about half (13/23) of the clones contained a cytidine residue at nucleotide position 65, while the other half (10/23) contained thymidine. The cDNA clone HRGR33 contained an insertion of 12 nucleotides, TGTCTCCCACAG (SEQ ID NO:7) between nucleotide positions 274 and 275 corresponding to the insertion of four amino acid residues, Val-Ser-His-Arg (SEQ ID NO:8) in the deduced amino acid sequence. Amino acid residues (three-letter code) in human and bovine retinaldehyde binding protein that conform to conserved sequence motifs in G protein-coupled receptors include $Asn^{34}$, $Asp^{62}$, $Cys^{88}$, $Arg^{113}$-$Tyr^{114}$, $Trp^{136}$, $Cys^{162}$ $Pro^{188}$, $Tyr^{196}$, $Trp^{224}$, $Pro^{226}$-$Tyr^{227}$, $Asn^{261}$, and $Tyr^{265}$.

FIGS. 7A and 7B show the nucleotide sequence of the human rgr gene (SEQ ID NO: 19–25). The intervening sequences are shown in lowercase letters. The major transcriptional initiation site is indicated in superscript and is numbered as +1. Only the exonic sequence is numbered on the right, and the 5'-flanking sequence is numbered negatively on the left. The underlined nucleotide sequence at the 3' end of intron 2 was found as an insertion in the human retinaldehyde binding protein cDNA clone HRGR33. A polyadenylation cleavage site is indicated by the backslash (\). The deduced amino acid sequence is written below the coding DNA sequence.

DETAILED DESCRIPTION OF PREFERRED EMBODIMENTS

Figure 2:
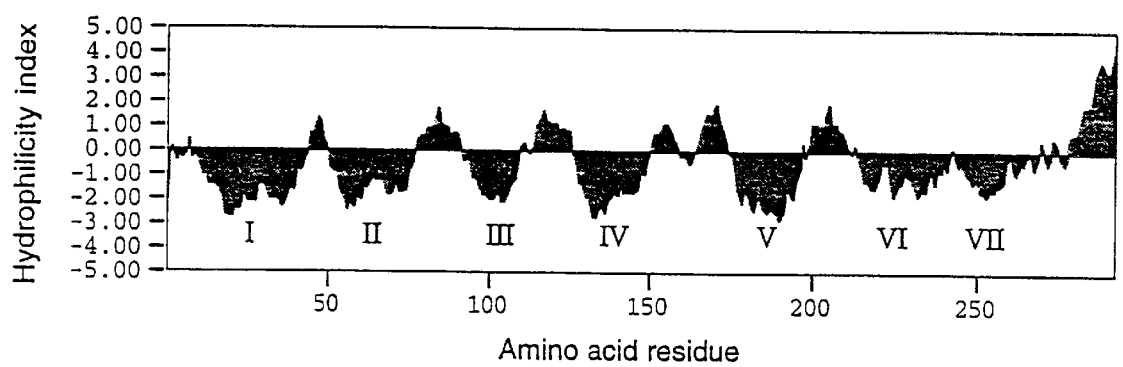
FIG. 2 shows hydrophilicity profile of the amino acid sequence of bovine retinaldehyde binding protein. Hydrophilicity analysis of the translated retinaldehyde binding protein sequence revealed the presence of seven distinct hydrophobic regions. The positions of the hydrophobic segments I–VII are indicated. The analysis was performed according to the Kyte-Doolittle hydrophilicity scale using a window setting of 10 amino acids. Hydrophobicity increases with decreasing values.

The present invention concerns a novel retinaldehyde-binding protein, which has distant homology to other G protein coupled receptors, such as opsin, tachykinin, serotonin, and muscarinic receptors, having seven (heptahelical) transmembrane domains. This novel retinaldehyde binding protein is the first light-absorbing vertebrate protein identified to stably and preferentially bind the all-trans-retinal chromophore. As a putative G protein coupled receptor, the retinaldehyde binding protein of the present invention is sometimes denominated retinal G protein coupled receptor or RGR.

The present invention also includes a naturally occuring variant of retinaldehyde binding protein wherein at least one amino acid residue in the polypeptide has been conservatively replaced by a different amino acid.

An amino acid or nucleic acid sequence of a retinaldehyde binding protein of the present invention is said to "essentially correspond" to another amino acid or nucleic acid sequence, respectively, if the sequence of amino acids or nucleic acids in both molecules provides or encodes polypeptide having all trans-retinal binding activity. Such "essentially corresponding" retinaldehyde binding protein sequences include these which have conservative amino acid or nucleotide substitutions, or degenerate nucleotide codon substitutions wherein individual amino acid or nucleotide substitutions are well known in the art.

Accordingly, retinaldehyde binding proteins of the present invention, or nucleic acid sequence encoding therefor, include a finite set of essentially corresponding sequences as substitution peptides or polynucleotides which can be routinely obtained by one of ordinary skill in the art, without undue experimentation, based on the teachings and guidance presented herein. For a detailed description of protein chemistry and structure, see Schulz, G. E. et al., Principles of Protein Structure, Springer-Verlag, New York, 1978, and Creighton, T. E., Proteins: Structure and Molecular Properties, W. H. Freeman & Co., San Francisco, 1983, which are hereby incorporated by reference. For a presentation of nucleotide sequence substitutions, such as codon preferences, see Ausubel et al, eds, CURRENT PROTOCOLS IN MOLECULAR BIOLOGY, Greene Publishing Assoc., N.Y., N.Y. (1987, 1988, 1989, 1990, 1991, 1992, 1993, 1994) at §§ A.1.1–A.1.24, and Sambrook et al, Molecular Cloning: A Laboratory Manual, Second Edition, Cold Spring Harbor Press, Cold Spring Harbor, N.Y. (1989), at Appendices C and D.

Based on the 86% homology observed between the amino acid sequence of the bovine and the human retinaldehyde binding protein, a person of skill in the art would readily recognize the criticality of certain amino acids in view of their homology to other G protein coupled receptor, particularly, those of visual pigments. Since other G protein coupled receptors are only distantly related, the shared homology with either bovine or human retinaldehyde binding protein is lower than between the bovine and human retinaldehyde binding protein of the present invention. Using this homology to identify conserved amino acid residues (such as the hydrophilic lysine residue in the seventh transmembrane domain) one of skill in the art would have a range of varying homology to determine the criticality of specific residues and domains. Armed with this information, a person of skill in the art can readily identify conserved and non-conserved amino acids and make amino acids substitutes accordingly.

Conservative substitutions of a retinaldehyde binding protein of the present invention include variants wherein at least one amino acid residue in the polypeptide has been conservatively replaced by a different amino acid.

Such substitutions preferably are made in accordance with the following list as presented in Table I, which substitutions can be determined by routine experimentation to provide modified structural and functional properties of a synthesized or recombinant polypeptide molecule, while maintaining all trans-retinaldehyde binding activity, as determined by retinaldehyde binding assays. In the context of the present invention, the term "essentially corresponding to" includes such substitutions.

TABLE 1

| Original Residue | Exemplary Substitution |
| --- | --- |
| Ala | Gly; Ser |
| Arg | Lys |
| Asn | Gln; His |
| Asp | Glu |
| Cys | Ser |
| Gln | Asn |
| Glu | Asp |
| Gly | Ala; Pro |
| His | Asn; Gln |
| Ile | Leu; Val |
| Lys | Arg; Gln; Glu |
| Met | Leu; Tyr; Ile |
| Phe | Met; Leu; Tyr |
| Ser | Thr |
| Thr | Ser |
| Trp | Tyr |
| Tyr | Trp; Phe |
| Val | Ile; Leu |

Accordingly, based on the above example of specific substitutions, alternative substitutions can be made by routine experimentation, to provide alternative retinaldehyde binding proteins of the present invention, e.g., by making one or more conservative substitutions.

Alternatively, another group of substitutions of retinaldehyde binding proteins of the present invention are those in which at least one amino acid residue in the protein molecule has been removed and a different residue inserted in its place according to the following Table 2. The types of substitutions which can be made in the protein or peptide molecule of the present invention can be based on analysis of the frequencies of amino acid changes between a homologous protein of different species or conserved amino acids between the human and bovine retinaldehyde binding proteins. Based on such an analysis, alternative conservative substitutions are defined herein as exchanges within one of the following five groups:

TABLE 2

| | |
| --- | --- |
| 1. | Small aliphatic, nonpolar or slightly polar residues: Ala, Ser, Thr (Pro, Gly) ; |
| 2. | Polar, negatively charged residues and their amides: Asp, Asn, Glu, Gln; |
| 3. | Polar, positively charged residues: His, Arg, Lys; |
| 4. | Large aliphatic, nonpolar residues: Met, Leu, Ile, Val, (Cys) ; and |
| 5. | Large aromatic residues: Phe, Tyr, Trp. |

The three amino acid residues in parentheses above have special roles in protein architecture. Gly is the only residue lacking any side chain and thus imparts flexibility to the chain. This, however, tends to promote the formation of secondary structure other than α-helices. Pro, because of its unusual geometry, tightly constrains the chain. It generally tends to promote β-turn-like structures. In some cases Cys can be capable of participating in disulfide bond formation which is important in protein folding. Note that Schulz et al. would merge Groups 1 and 2 above. Note also that Tyr, because of its hydrogen bonding potential, has significant kinship with Ser, and Thr, etc. Knowledge of the secondary structure and of the tertiary structure will assist those of ordinary skill in the art in determining which such substitutions would not be expected to affect binding.

Conservative amino acid substitutions, included in the term "essentially corresponding", according to the present invention, e.g., as presented above, are well known in the art and would be expected to maintain the binding properties of the polypeptide after amino acid substitution.

The present invention is directed not only to retinaldehyde binding peptides having a sequence corresponding or essentially corresponding to native retinaldehyde binding protein, but also to functional derivatives thereof.

By "functional derivative" is meant a derivative which retains at least the retinaldehyde binding function of the peptide which permits its utility in accordance with the present invention.

A "functional derivative" of the retinaldehyde binding protein may contain additional chemical moieties not normally a part of the peptide. Covalent and/or non-covalent modifications of the chemical derivativitized peptide are also included within the scope of this invention. Such modifications can be introduced into the molecule by reacting targeted amino acid residues of the peptide with an organic derivatizing agent that is capable of reacting with selected side chains of the residues or terminal amino groups. Covalent modifications of the retinaldehyde binding protein of the present invention are included within the scope of the functional derivatives which are part of the present invention. Such modifications can be introduced into the molecule by reacting targeted amino acid residues of the retinaldehyde binding protein with an organic derivatizing agent that is capable of reacting with selected side chains or N-terminal residues of the retinaldehyde binding protein.

Derivatization with bifunctional agents is useful for crosslinking the retinaldehyde binding protein or peptide fragment to a water-insoluble support matrix or surface, or to reactive water-insoluble matrices such as cyanogen bromide-activated carbohydrates, dextrans and/or their reactive substrates, e.g., described in U.S. Pat. Nos. 3,969,287; 3,691,016; 4,195,128; 4,247,642; 4,229,537; and 4,330,440 and employed for protein immobilization.

Most deletions, insertions and substitutions of retinaldehyde binding proteins according to the present invention are those which maintain or improve the retinaldehyde binding characteristics of the protein or peptide molecule. However, when it is difficult to predict the exact effect of the substitution, deletion, or insertion in advance of doing so, one skilled in the art will appreciate that the effect will be evaluated by routine screening assays. For example, a variant made by site-specific mutagenesis of the protein peptide molecule-encoding nucleic acid and expression of the variant retinaldehyde binding protein or peptide in cell culture or, alternatively, by chemical synthesis, can be tested for binding by binding assays disclosed herein, to test retinaldehyde binding capability.

Amino acid sequence variants of the retinaldehyde binding protein can also be prepared by mutations in the DNA. Such variants include, for example, deletions from, or insertions or substitutions of, residues within the amino acid sequence. Any combination of deletion, insertion, and substitution can also be made to arrive at expressing and producing the final peptide construct, provided that the final peptide construct possesses some retinaldehyde binding activity. Preferably improved retinaldehyde binding activity will be found over that of the non-variant peptide. Obviously, the mutations that will be made in the DNA encoding the variant must not place the sequence out of reading frame and preferably will not create complementary regions that could produce secondary mRNA structure (see, e.g., EP Patent Application Publication No. 75,444; Ausubel, supra; Sambrook, supra).

At the genetic level, these variants ordinarily are prepared by site-directed mutagenesis of nucleotides in the DNA encoding the retinaldehyde binding protein, thereby producing DNA encoding the variant, and thereafter synthesizing the DNA and expressing the protein in recombinant cell culture. The variants typically exhibit the same qualitative biological activity as the naturally occurring analogue, Ausubel, supra; Sambrook, supra.

It is intended that the present amino acid sequence of retinaldehyde binding proteins of the present invention be at least 65% homologous to the bovine and human retinaldehyde binding protein sequence presented herein, preferably at least: 75% homologous, and most preferably at least 85% homologous. It should be understood when the term "antibodies" is used with respect to the antibody embodiments of the present invention, this is intended to include intact antibodies, such as monoclonal or polyclonal antibodies, as well as proteolytic fragments thereof such as the Fab or $F(ab')_2$ fragments. Furthermore, the DNA encoding the variable region of the antibody can be inserted into other antibodies to produce chimeric antibodies (see, for example, U.S. Pat. No. 4,816,567) or into T-cell receptors to produce T-cells with the same broad specificity (see Eshhar, Z. et al., Br. J. Cancer Suppl., 10:27–9 (1990); Gross, G. et al., Proc. Natl. Acad. Sci. USA, 86:10024–8 (1989)). Single chain antibodies can also be produced and used. Single chain antibodies can be single chain composite polypeptides having antigen binding capabilities and comprising a pair of amino acid sequences homologous or analogous to the variable regions of an immunoglobulin light and heavy chain (linked $V_H$–$V_L$ or single chain $F_v$). Both $V_H$ and $V_L$ may copy natural monoclonal antibody sequences or one or both of the chains may comprise a CDR-FR construct of the type described in U.S. Pat. No. 5,091,513 (the entire contents of which are hereby incorporated herein by reference). The separate polypeptides analogous to the variable regions of the light and heavy chains are held together by a polypeptide linker. Methods of production of such single chain antibodies, particularly where the DNA encoding the polypeptide structures of the $V_H$ and $V_L$ chains are known, may be accomplished in accordance with the methods described, for example, in U.S. Pat. Nos. 4,946,778, 5,091, 513 and 5,096,815, the entire contents of each of which are hereby incorporated herein by reference.

A molecule which includes the antigen-binding portion of an antibody, is intended to include not only intact immunoglobulin molecules of any isotype and generated by any animal cell line or microorganism, but also the reactive fraction thereof including, but not limited to, the Fab fragment, the Fab' fragment, the $F(ab')_2$ fragment, the variable portion of the heavy and/or light chains thereof, and chimeric or single-chain antibodies incorporating such reactive fraction, as well as any other type of molecule or cell in which such antibody reactive fraction has been physically inserted, such as a chimeric T-cell receptor or a T-cell having such a receptor, or molecules developed to deliver therapeutic moieties by means of a portion of the molecule containing such a reactive fraction.

Preparation of Bovine RPE RNA and Construction of an RPE cDNA Library

Bovine RPE cells were isolated and RNA was prepared within two hours of eye enucleation. After excision of the anterior segment and removal of the lens, vitreous and neurosensory retina, RPE cells were isolated by enzymatic digestion with 50 units/ml of hyaluronidase and 100 units/ml of collagenase, followed by gentle scraping of the cell monolayer. The RPE cells were collected by centrifugation and homogenized immediately in 4 M guanidinium thiocyanate. Total cell RNA was prepared by acid guanidinium thiocyanate-phenol-chloroform extraction (Chomczynski et al., Anal. Biochem., 162: 156–159, 1987). Poly(A)+RNA was selected by binding to oligo(dT)-cellulose. The yield of RPE poly(A)+RNA was about 1 μg per 20 bovine eyes, and the preparation showed about 20% contamination with RNA from the neurosensory retina. The level of contamination of the RPE RNA with retinal RNA was estimated by hybridization to a bovine transducin γ subunit cDNA probe. A cDNA library was constructed using the RPE-enriched poly (A)+RNA and the bacteriophage λgt10 vector, according to published methods (Gubler et al., Gene, 25: 263–269, 1983; DNA Cloning, A Practical Approach, IRL Press, p. 49–78, 1985). The library contained a total of about 150,000 recombinant clones.

Isolation and Characterization of RPE cDNA Clones

The RPE cDNA library was screened for tissue-specific cDNAs by differential plaque hybridization to radiolabeled bovine RPE and kidney cDNA probes that were synthesized with reverse transcriptase from poly(A)+RNA. Due to a 10–20% contamination of the RPE RNA with retina RNA, several distinct clones that hybridized specifically to retina mRNA were isolated. In general, the selected clones encoded a relatively abundant species of mRNA, as expected from the approach used in the screening process. On Northern blots, the cDNA clone, RPE6, hybridized much more strongly to RPE-enriched RNA than to retina RNA. The library was rescreened with RPE6 cDNA to isolate the overlapping cDNA clone, RPE12. The RPE6 and RPE12 cDNA inserts were subcloned into pBluescript vector (Stratgene, La Jolla, Calif.), and both strands of the inserts were sequenced using the dideoxy chain termination method.

RNA Blot Hybridization

Total RNA from RPE cells and retina was isolated by acid guanidinium thiocyanate-phenol-chloroform extraction. RNA from other tissue samples was prepared from quick-frozen tissue by guanidinium thiocyanate extraction and LiCl precipitation (Cathala et al., DNA, 2:329–335, 1983). Poly(A)+RNA was isolated by binding to oligo(dT)-cellulose columns. The RNA was electrophoresed in 0.9% agarose gels containing 2.2 M formaldehyde and then transferred to nitrocellulose. The filter was hybridized for 24 hrs at 42° C. in buffer containing 50% formamide, 5×SSC, 50 mM $NaH_2PO_4$, pH 7.0, 2×Denhardt's solution, 0.1% SDS, 50 μg/ml of denatured salmon sperm DNA, and cDNA probe ($10^6$ count/min/ml). The probes were derived from cDNA clone RPE6 and human G-protein $\alpha_{11}$-subunit cDNA and were labelled by nick translation. The final washing of the filter was performed in a solution containing 0.1×SSC and 0.1% SDS at 54° C. for 30 min. Autoradiography was accomplished by exposure to Kodak X-omat AR film at −80° C. using an intensifying screen.

Isolation of Preferentially Expressed RPE cDNA Clones

A bovine RPE cDNA library in bacteriophage λgt10 was screened for RPE-specific clones by differential hybridization to radiolabeled bovine RPE and kidney cDNA probes. Forty candidate cDNA clones were identified as having hybridized to the RPE probe, but not to the kidney probe, and 10 of these were selected for further analysis by Northern blot hybridization. One of the selected cDNA clones, clone RPE6, hybridized to a 1.5 kb mRNA transcript that was seen in RNA from RPE, retina and brain, but not in RNA from other tissues. A larger transcript, 3.4 kb in length, also hybridized prominently in RPE RNA. This larger mRNA was observed in retina RNA only after longer exposure, and it was not detected in brain RNA. The RPE6 cDNA clone contained a 1.3 kb insert that corresponded to an mRNA that is highly expressed in the RPE, and that is expressed also in the retina and brain; however, it is barely detectable in the brain by Northern blot hybridization.

After rescreening the RPE cDNA library with the 1.3 kb cDNA as a probe, a clone with a longer cDNA insert and with an overlapping sequence (clone RPE12) was obtained. About 0.2% of the clones in the cDNA library cross-hybridized to the 1.3 kb cDNA probe under conditions of high stringency. Thus, the selected clone encoded an abundant species of RPE mRNA, as expected from the differential hybridization strategy used in the screening process. The nucleotide sequence derived from the two overlapping cDNA clones is 1410 nucleotides long (SEQ ID NO:1), excluding the poly(A) tail (FIG. 1). It was not identical to any of the nucleotide sequences within the GenBank database, release 74.0. The nucleotide sequence search was performed using the BLAST network service at the National Center for Biotechnology Information (NCBI).

Sequence of a Novel Retinaldehyde Binding Protein

The conceptual translation of the cDNA sequence yielded a long open reading frame of 291 amino acid residues with a cumulative molecular weight of 31,959 (FIG. 1). The putative initiation codon is the 5'-most ATG triplet of the cDNA sequence and is found in the context of a consensus translational start site. No signal peptide sequence was found at the predicted amino terminus. A desktop computer search of the protein sequence database, Protein Identification Resource release 31.0, was conducted to identify homologous matches to the deduced amino acid sequence. A protein sequence similarity search was also performed using the BLAST network service. The searches resulted in best matches to a long list of known G protein-coupled receptors. The translated amino acid sequence showed homology to opsin, tachykinin, serotonin, and muscarinic receptors, all of which belong to the family of receptors having seven putative transmembrane domains. Within the family of heptahelical receptors, the query sequence was most highly conserved with members of the visual pigment lineage. It is about 25% homologous and, taking into consideration the conservative amino acid substitutions, has 42% homology to the sequence of bovine opsin. Its hydrophilicity plot (FIG. 2) and sequence alignment with bovine opsin do suggest the presence of seven hydrophobic segments in the novel amino acid sequence, each segment approximately 25 amino acids in length. As in bovine opsin, the cytoplasmic interfaces of the assigned transmembrane segments are consistently demarcated by or positioned close to a positively charged amino acid residue.

Glycosylation and intrachain disulfide bond formation are common post-translational modifications of G protein-coupled receptors. A consensus sequence for potential glycosylation is located at $Asn^{172}$ in the assumed second extracellular loop of the novel protein, but none are found in the amino terminal region. Conserved disulfide bond formation involves cysteine residues located in the first and second extracellular loops of the heptahelical receptors (Jackson, *Pharmac. Ther.*, 50:425–442, 1991). These potential sites for the common intrachain disulfide bond are conserved at Cys$^{88}$ and Cys$^{162}$ in the deduced amino acid sequence. The third cytoplasmic loop and carboxyl tail of the novel sequence contain several hydroxyl amino acids, some of which may be sites for regulatory phosphorylation. Since it contains homologous features and sequence motifs consistent with the structure of G protein-coupled receptors, the putative receptor may be an RPE-retinal G protein-coupled receptor, but is denoted and referred to herein as retinaldehyde binding protein.

Expression of the rgr Gene and the Encoded Retinaldehyde Binding Protein

To verify the expression of retinaldehyde binding protein in the RPE, in situ hybridization with retinaldehyde binding protein anti-sense RNA probes was performed using frozen sections of the tapetal region of normal bovine retina, where the RPE is amelanotic.

An amelanotic portion of bovine retina with attached choroid complex was embedded in OCT compound (Miles, Inc., Elkhart, Ind.), frozen slowly in liquid nitrogen, and stored at −80° C. until sectioning. Retina sections of 10 μm were cut with a cryostat, thaw-mounted onto slides, and kept frozen until used for hybridization. The sections were fixed in 4% paraformaldehyde in phosphate-buffered saline (PBS) for 30 minutes at room temperature, and then rinsed sequentially in PBS, water and 0.1 M triethanolamine, pH 8.0. Acetylation was carried out at room temperature for 10 min in a solution containing 0.25% acetic anhydride, 0.1 M triethanolamine, and 0.9% NaCl. The tissue sections were dehydrated by rinsing stepwise with ethanol at increasing concentrations. In situ hybridization was performed using $^{35}$S-labelled RNA probes. The antisense and sense RNA probes were synthesized and labelled in vitro using T3 and T7 RNA polymerases to transcribe the RPE6 cDNA in the pBluescript vector. Hybridization of the tissue sections was performed in a buffer containing 50% formamide, 4×SSC, 5×Denhardt's solution, 1% SDS, 0.25 μg/ml yeast tRNA, 10% dextran sulfate, 0.1 M DTT, 25 μg/ml poly A, and 25 μg/ml poly C. The hybridization was carried out for 3 hrs at 50° C. in a humidified environment. The probes were heated at 70° C. for 5–10 min before adding to the sections at about 5×10$^5$ cpm/section. After hybridization the sections were treated with 20 mg/ml RNase A for 30 min at 37° C., washed in 2×SSC/20 mM β-mercaptoethanol at 22° C. for at least 2 hrs, and in 50% formamide/0.5×SSC/1 mM EDTA/5 mM DTT at 55° C. for 45 min. The slides were rinsed with 0.3 M ammonium acetate before drying and coating with Kodak (Rochester, N.Y.) NTB-2 nuclear track emulsion. After exposure at 4° C. for 12 days, the slides were developed in Kodak Dektol, stained with toluidine blue, and mounted in permount.

The resulting autoradiogram revealed a highly specific pattern of retinaldehyde binding protein mRNA expression within the retina. The antisense probe hybridized to the RPE cells, the inner nuclear layer, and specific cells in the ganglion cell layer, but did not appear to hybridize to the photoreceptors. No signals were seen in the vascular endothelial cells. In the control experiment, hybridization with the sense RNA probe resulted in a low homogeneous background. The results demonstrate that retinaldehyde binding protein is expressed in the inner retina as well as in the RPE; however, the specific cell type in the inner retina is difficult to distinguish by in situ hybridization.

For investigation of the protein product of the rgr gene, antibodies were raised against a synthetic peptide corresponding to the carboxyl terminal amino acid sequence of retinaldehyde binding protein (amino acid residues 279–291 of SEQ ID NO:2). This 13 amino acid long peptide, which corresponds to the carboxyl terminus of bovine retinaldehyde binding protein, a putative heptahelical receptor, was synthesized using an Applied Biosystems automated peptide synthesizer and conjugated to keyhole limpet hemocyanin. The production of antibody in rabbits was carried out by Cocalico Biologicals, Reamstown, Pa. The antipeptide antibodies (bcDE ½) were affinity-purified by immunoadsorption to the cognate peptide, coupled to CNBr-activated Sepharose (Pharmacia LKB Biotechnology, Piscataway, N.J.).

For immunoblot analysis, bovine tissues were homogenized using a Brinkmann polytron at the no. 5 setting for 30 seconds in a buffer containing 10 mM sodium phosphate, pH 7.0, 1 mM EDTA, 250 mM sucrose, and 0.2 mM phenylmethylsulfonyl fluoride. Protein concentrations were measured using Bio-Rad protein assay reagents (Bio-Rad Laboratories, Richmond, Calif.). For each tissue, 100 μg of total cell protein was electrophoresed in duplicate 12.5% SDS polyacrylamide gels. After electrophoresis, one gel was stained with 0.5% Coomassie blue, and the duplicate gel was submitted to electrophoretic transfer of proteins onto nitrocellulose filter. The protein blot was incubated first with the affinity-purified antipeptide antibody, and then with secondary antibody, alkaline phosphatase-conjugated goat antibody against rabbit IgG. The binding assay was developed with the substrates, nitro blue tetrazolium and 5-bromo-4-chloro-3-indolyl phosphate.

On Western blots, the affinity-purified antipeptide antibody recognized predominantly a 32-kD protein in bovine retina and RPE cell extracts, but not in extracts from other tissues (e.g. kidney, heart, lung, liver). The recognized protein agrees in size with the calculated molecular weight of the deduced retinaldehyde binding protein, and the distribution of the recognized protein is consistent with the pattern of retinaldehyde binding protein mRNA expression. In addition, the staining of this protein from the RPE was strong. Although the signal for the neural retinal extract was weak in comparison to the signal from the RPE extract, the relative signal intensities for neural retina and RPE may be skewed by the inclusion of a large amount of photoreceptors and other non-expressing cells in extracts from the neural retina.

The affinity-purified antibody (bcDE ½) was used to localize retinaldehyde binding protein in bovine retina by immunohistochemistry.

Bovine eyes were obtained postmortem from a local abattoir. After removal of the anterior segment and vitreous humor, the eye cup was immersed for two hours at 4° C. in 4% paraformaldehyde in PBS. The tissue was then infiltrated overnight with cryoprotectant 30% sucrose in PBS. The central tapetal region of the retina containing amelanotic RPE cells was dissected from the choroid and sclera, embedded in OCT compound (Miles, Inc.), and frozen. The frozen tissue was sectioned with a cryostat at −20° C. to a thickness of 10 μm, and mounted on Superfrost/Plus slides (Fisher Scientific, Pittsburgh, Pa.). For immunohistochemistry, the air-dried sections were preincubated with blocking reagent consisting of 4% goat serum, 1% BSA, and 0.4% Triton X-100 in PBS. The sections were then incubated for two hours with primary antibody diluted 1:250 in PBS containing 1% goat serum, 1% bovine serum albumin, and 0.2% Triton X-100. The control sections were treated identically, except that the primary antibody was preincubated with 600 μg/ml peptide in excess to block the antibody binding sites.

After washing, the sections were incubated with biotinylated goat anti-rabbit antibody. The bound antibodies were detected by incubation with a complex of avidin and biotinylated horseradish peroxidase from the Vectastain system (Vector Laboratories, Burlingame, Calif.), and assayed in a solution of the chromogen substrate, 0.04% 3-amino-9-ethylcarbazole and 0.01% $H_2O_2$.

Frozen sections were prepared from bovine eyes that were light-adapted and from regions of the retina in which the RPE monolayer was amelanotic. The retinal pattern of staining obtained with the antibody to retinaldehyde binding protein was intrinsically specific, and the RPE monolayer was intensely positive. In addition to the positive signal in the RPE, staining was observed in the region close to the inner limiting membrane and in cellular processes that extend from this region to the inner nuclear layer. This reproducible staining in the inner retina best represented localization to Müller cell processes and their basal end feet. The result is compatible with the in situ identification of hybridizing mRNA in the inner nuclear layer, where Müller cell nuclei reside. In the control, immunohistochemical staining was absent when the antibody was preincubated with excess peptide.

Antibody Specificity and Immunoblot Analysis of Bovine Retinaldehyde Binding Protein To study the localization of retinaldehyde binding protein in the retina, we generated rabbit antisera against synthetic peptides that correspond to the amino terminal amino acid sequence (amino acid residues 2–16 of SEQ ID NO:2 with an added cysteine following residue 16) and carboxyl terminal amino acid sequence (amino acid residues 279–291 of SEQ ID NO:2) of bovine retinaldehyde binding protein. These peptides were synthesized using an automated peptide synthesizer and then conjugated to keyhole limpet hemocyanin (KLH). The production of antibody in rabbits was carried out by Cocalico Biologicals, Reamstown, Pa. Antipeptide antisera were generated by immunizing rabbits with 100 µg KLH-conjugated peptide mixed with an equal volume of complete Freund's adjuvant. The rabbits were boosted 14 and 21 days later with 50 µg immunogen mixed with an equal volume of incomplete Freund's adjuvant. Immunoreactivity of the antisera was tested by enzyme-linked immunosorbent assay, following methods described previously (Engvall et al., *Immunochem.*, 8:871–879, 1971). Peptides conjugated to ovalbumin were immobilized onto 96-well plates. The bound antipeptide antibodies were detected using goat anti-rabbit IgG conjugated to horseradish peroxidase and o-phenylene-diamine substrate solution. The antibodies were affinity-purified by binding to the cognate peptide coupled to CNBr-activated Sepharose 6 MB column (Pharmacia Biotech Inc., Piscataway, N.J.), according to published procedures (Mumby et al., *Meth. Enzymol.*, 195, 1991).

The affinity-purified antibodies were characterized by immunoblot analysis of proteins from bovine RPE, retina, and other tissues. Bovine RPE, retina, brain, and other tissues were homogenized using a Brinkmann polytron. The homogenization buffer contained 10 mM sodium phosphate, pH 7.0, 250 mM sucrose, 1 mM EDTA and 0.2 mM phenylmethylsulfonyl fluoride. The homogenates were centrifuged at 800 g to remove unbroken cells and debris, and centrifuged again at 150,000 g for 1 hour to obtain crude membrane and soluble protein fractions. The supernatants were used as soluble protein samples, and the membrane pellets were resuspended in homogenization buffer. The RPE membrane pellet was also extracted in buffer containing 1.2% digitonin, 15 mM sodium phosphate buffer, pH 6.5, and 1 mM EDTA. The digitonin-containing extract was centrifuged at 150,000 g to obtain solubilized RPE membrane proteins in the high-speed supernatant. Protein concentrations were measured by the Bio-Rad protein assay (Bio-Rad Laboratories, Richmond, Calif.).

Membranes and soluble proteins from bovine tissues were electrophoresed in 12.5% SDS-polyacrylamide gels. The samples were boiled, and electrophoresis of proteins was performed according to Laemmli, *Nature*, 227:680–685, 1970. After electrophoresis, the proteins were transferred to nitrocellulose membranes for immunoblot analysis. The blots were incubated overnight with 5% skim milk in Tris-buffered saline and then incubated sequentially with primary antibodies to retinaldehyde binding protein peptides and anti-rabbit IgG that had been conjugated to alkaline phosphatase. The detection of bound antibodies was achieved using nitro blue tetrazolium (NBT) and 5-bromo-4 chloro-3 indolyl phosphate (BCIP) as the chromogen substrates. Protein standards were included as molecular weight markers.

The antibodies against the amino (bnDE ¾) and carboxyl (bcDE ½) terminal sequences of retinaldehyde binding protein each recognized a 32-kD protein from bovine retina and RPE. The amino terminal antibody detected a single 32-kD protein from retina and RPE membranes, but not in membranes from other tissues. This result is in agreement with previous results obtained with the carboxyl terminal antibody and verifies binding of the antibodies to the retinaldehyde binding protein. Smaller peptide fragments were not detected in freshly prepared RPE cell extracts.

The subcellular distribution of retinaldehyde binding protein was analyzed by fractionation of RPE and retina by centrifugation. After high speed centrifugation of the tissue homogenates at 150,000 g, retinaldehyde binding protein was detected in the pellets containing membrane fractions of RPE or retina, but not in the supernatants containing soluble cytosolic proteins. Digitonin as a surface active agent could be included in a buffer to solubilize retinaldehyde binding protein from RPE membranes. Other suitable surface agents, such as dodecyl maltoside, that solubilize retinaldehyde binding protein without denatuation and are well within the knowledge of those skilled in the art, can be used. These results show that retinaldehyde binding protein is a 32-kD protein bound to membranes or associated with subcellular particulates in the RPE and retina.

Immunocytochemical Localization of Retinaldehyde Binding Protein at the Light Microscopic Level The affinity-purified antibodies (bcDE ½ and bn DE ¾) were also characterized by immunohistochemistry using the horseradish peroxidase staining method. Bovine retinal sections were obtained from light-adapted eyes obtained from a local abattoir and were prepared from the tapetal region with amelanotic RPE, so that the pigment would not mask the staining of the RPE.

The anterior segment and vitreous humor were excised, and the eye cup was immersed in 4% paraformaldehyde in phosphate buffered saline (PBS). After two hours in fixative at 4° C., the eyes were infiltrated overnight with 30% sucrose in PBS. A portion of retina with amelanotic RPE was dissected from the choroid and sclera and embedded in OCT compound (Miles Inc., Elkhart, Ind.). The tissue was frozen and sectioned on a cryostat at a thickness of 10 µm.

For immunohistochemistry, the retinal sections were dried, rinsed in PBS, and incubated in a blocking solution of 4% goat serum, 1% BSA, and 0.4% Triton X-100 in PBS. The sections were then incubated with affinity-purified anti-peptide antibody diluted 1:250 in a PBS solution containing 1% goat serum, 1% BSA and 0.2% Triton X-100. Control sections were treated identically, except that the antibodies were preabsorbed with peptide antigen at 600 µg/ml. The sections were washed with PBS and incubated with biotinylated goat anti-rabbit antibody and then with a complex of avidin and biotinylated horseradish peroxidase, the ABC reagent (Vector Labs., Burlingame, Calif.). Specific antibody binding was visualized by incubation with a chromogen substrate solution of 0.04% 3 amino-9 ethylcarbazole and 0.01% $H_2O_2$. The tissue sections were counterstained with hematoxylin to provide nuclear detail.

The retina was stained by each of the two antibodies, one directed against the amino terminal and the other directed against the carboxyl terminal sequence of retinaldehyde binding protein. In controls, specific staining was not detected if the primary antibodies were preabsorbed with excess peptide. Both antibodies gave the same staining pattern. The RPE monolayer was intensely positive, and the antibodies stained the region close to the inner limiting membrane, including cell processes that projected radially upwards to the inner nuclear layer. Photoreceptors were negative. These results are consistent with the localization of retinaldehyde binding protein in RPE and in Müller cell processes and endfeet, which end at the inner limiting membrane. Cells in the inner nuclear layer were also stained, and these appeared to be Müller cell somata, due to their position in the middle to vitreal part of the inner nuclear layer.

Immunocytochemical Localization of Retinaldehyde Binding Protein at the Electron Microscopic Level Anterior segments of the bovine eyes were removed, and the eye cups were fixed for 30 minutes in 0.1 M cacodylate buffer, pH 7.4, containing 4% paraformaldehyde and 2% glutaraldehyde. The retina with attached RPE was peeled away from the choroid and sclera, cut into small pieces, and fixed again for 2 hours. Sections were washed in 0.1 M sodium cacodylate buffer, pH 7.4, dehydrated sequentially in 15%, 30%, and 50% ethanol, and stained with 2% uranyl acetate in 70% ethanol for 1 hour. The sections were dehydrated again in ethanol concentrations ranging from 85% to 100% and then embedded in LR white resin. Thin sections were cut to 70 nm thickness and placed on nickel grids.

For immunogold staining, the retinal thin sections on nickel grids were incubated for 1 hour in a blocking solution of 1% BSA in PBS. The grids were floated and rotated overnight at 4° C. on drops of the primary antibody, diluted 1:100 in PBS containing 0.1% BSA. This was followed by incubation with a 1:100 dilution of 10 nm gold-labeled goat anti-rabbit IgG (Amersham Corp., Arlington Heights, Ill.) for 5 hours at 23° C. The grids were washed with PBS, floated on Karnovsky's fixative (2% paraformaldehyde and 2% glutaraldehyde) for 10 minutes, and then washed with water. The sections were counterstained with uranyl acetate for 10 minutes, followed by lead citrate for 5 minutes. The grids were examined on a Zeiss EM-10 electron microscope (Thornwood, N.Y.).

The ultrastructural distribution of the retinaldehyde binding protein in the RPE and retina was studied by immunocytochemistry at the electron microscopic level. In these experiments, the antibody directed against the carboxyl terminus of retinaldehyde binding protein was used as the primary antibody. A goat anti-rabbit IgG conjugated with 10-nm gold particles was used as the secondary antibody. In the RPE cells, gold-labeling was detected prominently in the intracellular domain. The RPE cytoplasm was uniformly labeled throughout the cell, except for the region close to the basal infoldings. Due to the low contrast of cell profiles in non-osmicated tissue, it was difficult to identify precisely the subcellular structure to which the gold label was localized. The labeling was not localized specifically in the RPE plasma membrane, mitochondria, rough endoplasmic reticulum, or the nucleus. Labeling was present near the apical surface of the RPE, but there was only sporadic labeling of proximal portions of the apical microvilli. The RPE cytoplasm near the basal surface showed no immunoreactivity, and the RPE basal infoldings per se were not labeled by the antibody to retinaldehyde binding protein.

Gold particles were also localized in the area near the inner limiting membrane in cells identified morphologically as the Müller cells. Labeling was readily observed within the cytoplasm of the Müller cell endfeet and radiating cell processes. The processes and endfeet of the Müller cells were identified by their position relative to the basal lamina of the inner limiting membrane or by the presence of many intermediate filaments. As in the RPE, the retinaldehyde binding protein was detected in an intracellular compartment. No labeling was observed in the control experiments in which the affinity-purified antibody was omitted in the incubation buffer.

Binding of All-trans- and 11-cis-retinal to Bovine Retinaldehyde Binding Protein The hypothesis that retinaldehyde binding protein is a receptor for one or more isomers of retinal was tested by analysis of the covalent binding of [$^3$H]-labeled all-trans- and 11-cis-retinal to bovine RPE microsomal proteins. A preparation of RPE microsomes was first exposed to light for one hour in an attempt to photobleach retinaldehyde binding protein that may be bound endogenously to retinal. Equal aliquots of the membrane suspension were then incubated in the dark with either all-trans [$^3$H]- or 11-cis [$^3$H]-retinal. After the incubation, sodium borohydride was added to the microsomes, and the membranes were then either kept in the dark or immediately irradiated for 5 min. The labeling of proteins in the microsomes was analyzed by fluorography after SDS-polyacrylamide gel electrophoresis.

The protocol for the above experiment is described below. All-trans[11,12-$^3$H]-retinal was prepared by chemical oxidation of [11,12-$^3$H]-retinol (40–60 Ci/mmol), according to Ball et al. *Biochem. J.*, 42: 516–523, 1948. The [11,12-$^3$H]-retinol (250 mCi) was oxidized in the presence of 2.4 mg $MnO_2$ in a hexane solution saturated with retinoic acid. The reaction was performed for 2 hours in the dark under a nitrogen atmosphere, and the products of the reaction were filtered through a GF/C glass filter. The all-trans[11,12-$^3$H]-retinal was isolated by HPLC and used to prepare 11-cis [11,12-$^3$H]-retinal by photoisomerization. The irradiation of purified all-trans[11,12-$^3$H]-retinal in ethanol by a fiber optic light source for 5 min resulted in an isomeric mixture containing 13-cis-, 11-cis-, 9-cis-, and all-trans-retinals. The all-trans- and 11-cis[11,12-$^3$H]-retinal isomers were isolated and routinely analyzed for purity by normal phase chromatography using a LiChrosorb RT Si60 silica column (4×250 mm, 5 µm) (E. Merck, Darmstadt, Germany) and a Bio-Rad HPLC system. The HPLC column was pre-calibrated using purified isomers of retinal. The standards were eluted with 2% dioxane in hexane as the mobile phase and detected by UV absorbance at 325 nm. The isolation of the labeled retinoids was based on elution times of the standards. The crystals of isomeric retinaldehyde standards were stored at −80° C. in a light-protected container before use.

The isolation of bovine RPE cells from postmortem bovine eyes and preparation of RPE microsomes were carried out under dim yellow or red light within two hours of enucleation. After excision of the anterior segment and removal of the lens, vitreous and neural retina, RPE cells were removed by gently scraping the cell monolayer with a spatula. The cells were collected by centrifugation and homogenized in ice-cold sucrose buffer of 0.25 M sucrose, 30 mM Tris-acetate, pH 7.0, and 1 mM DTT using a Dounce glass homogenizer. The homogenate was centrifuged at 300 g at 4° C. to remove nuclei and unbroken cells. The pellet was resuspended, and the homogenization and centrifugation steps were repeated four times. The combined supernatants from the homogenization steps were centrifuged in a Sorvall SS-34 rotor at 15,000 g for 20 min at 4° C. The 15,000 g supernatant contained the RPE microsome fraction from which the membranes were then collected by centrifugation in a Beckman 70 Ti rotor at 150,000 g for 1 hour at 4° C.

RPE microsomes from 10 bovine eyes were prepared as described above, and resuspended in 1.0 ml cold 67 mM sodium phosphate, pH 6.5 (protein conc.: 0.85 mg/ml). The membranes were exposed for 1 hour to light from a fiber optic light source, and then equal aliquots (0.25 ml) of the membrane suspension were mixed in the dark with 2.5 $\mu$l ethanolic solution of all-trans[$^3$H]- or 11-cis[$^3$H]-retinal (each isomer at 1×10$^5$ or 0.4×10$^5$ cpm, 50 Ci/mmol). The mixtures were incubated in the dark with gentle agitation for 3 hours at room temperature. After incubation the membranes were collected by centrifugation at 38,500 rpm for 25 min at 4° C. using a Beckman SW60 rotor. The pellet was washed three times and resuspended in 1.0 ml of 67 mM sodium phosphate, pH 6.5. After adjustment of the buffer pH to 8.0 with 1 M NaOH, the membrane suspension was mixed with 38 mg sodium borohydride (1 M NaBH$_4$, final concentration) and then immediately irradiated for 5 min by a flood lamp light source. The membranes were recovered again by centrifugation and washed three times with phosphate buffer. The above experiment was repeated, except that the sodium borohydride reaction and all subsequent washing steps were carried out completely in the dark. Labeled microsomal proteins were analyzed by fluorography after SDS-PAGE. For fluorography, the 12% polyacrylamide gel was saturated with Enlightning reagent (Dupont NEN Research Products, Boston, Mass.), dried, and exposed to Kodak X-omat AR film at −80° C. for a period of 5 days.

Although added to a highly complex mixture of membrane proteins, both all-trans[$^3$H]- and 11-cis[$^3$H]-retinal covalently bound and specifically labeled a single protein in the RPE microsomes, both under light and in the dark. The labeled protein was 32 kd, conforming to the bovine retinaldehyde binding protein in size. The degree of labeling was consistently greater with all-trans-[$^3$H]-retinal than with the 11-cis isomer. Exposure to light during the reduction step in the presence of sodium borohydride did not significantly affect the intensity of the bands. Although some rhodopsin was present as a contaminant, the labeled protein in RPE microsomes differed in size from rhodopsin, as detected by Western immunoblot.

The binding of retinal to retinaldehyde binding protein was confirmed by specific immunoprecipitation of the protein from RPE microsomes. A portion of RPE microsomes that were labeled covalently with all-trans[$^3$H]-retinal was solubilized in digitonin-containing phosphate buffer, and retinaldehyde binding protein in the soluble extract was immunoprecipitated using a monoclonal antibody directed against the carboxyl terminus of bovine retinaldehyde binding protein.

Specifically, after incubation with all-trans[11,12-$^3$H]-retinal and treatment with sodium borohydride, as described above, the RPE microsomal proteins were solubilized in a solution of 1.2%. digitonin and 67 mM sodium phosphate, pH 6.5. For each condition, the digitonin extract (200 $\mu$l) was added to 600 $\mu$l of binding buffer (500 mM NaCl and 10 mM sodium phosphate, pH 7.2) and 150 $\mu$l of immunoaffinity resin (described below). The mixtures were incubated at 4° C. for 2 hours in the presence or absence of excess blocking peptide. Two of the samples included a high concentration of bovine retinaldehyde binding protein, either 100 $\mu$M of amino terminal peptide or 100 $\mu$M of carboxyl terminal peptide. The immunobeads were washed in binding buffer containing 0.3% digitonin and recovered by centrifugation. Samples of the immunoprecipitates and original extract were analyzed by fluorography after electrophoresis in 12% SDS-polyacrylamide gels. The gel was exposed to Kodak X-omat AR film at −80° C. for a period of 8 weeks.

The immunoaffinity resin was conjugated with anti-bovine retinaldehyde binding protein monoclonal antibody 2F4, which was produced and purified as described below. The antibody-containing fractions from Mono Q chromatography were pooled and dialyzed three times in 0.1 M MOPS, pH 7.5, at 4° C. Activated Affi-Gel 10 resin (Bio-Rad, Hercules, Calif.) was added to the antibody solution, and the suspension was agitated gently for 4 hours at 4° C. After the coupling reaction, the gel was incubated for 1 hour in 0.1 M ethanolamine to block the remaining reactive sites. The immunoaffinity gel was then washed with water, equilibrated with binding buffer, and stored at 4° C. until use.

A monoclonal antipeptide antibody 2F4 was produced against the carboxyl terminal amino acid sequence of bovine retinaldehyde binding protein. Hybridomas were obtained from Susan K.-H. Ou (Division of Biology, Caltech, Pasadena, Calif.), and were produced according to Ou et al., *J. Immunol. Methods,* 145: 111–118, 1991. The synthetic peptide was conjugated to keyhole limpet hemocyanin, emulsified with RIBI adjuvant (RIBI Immunochemical Research, Hamilton, Mont.), and injected intraperitoneally into 5-week-old female BALB/c mice. Spleen cells from the immunized mice were fused with Myeloma-653 cells from Ventrex Laboratories, Inc. (Portland, Me.). The hybridomas were grown initially in selection medium containing RPMI 1640 supplemented with 1% fetal calf serum (Hyclone, Logan, Utah), 4 mM glutamine, 10 U/ml each of penicillin and streptomycin, 1 mM sodium pyruvate, 75 $\mu$M adenine, 0.4 $\mu$M aminopterin, and 16 $\mu$M thymidine. Immunoreactivities of the monoclonal antibodies and antisera were tested by enzyme-linked immunosorbent assay (ELISA) and by immunoblot analysis. Anti-retinaldehyde binding protein positive hybridoma cells were cloned by culturing single cells in HL-1 medium (Ventrex Laboratories, Inc.), containing 1% fetal bovine serum, 200 mM glutamine, and 10 U/ml each of penicillin and streptomycin. The hybridoma clones were grown on a lawn of BALB/c thymus feeder cells at 37° C. in a humidified air atmosphere of 5% $CO_2$.

The hybridoma clone 2F4 cells were grown in large scale in HL-1 or UltraDOMA-PF (BioWhittaker, Inc., Walkersville, Md.) medium that contained 1% fetal bovine serum, 200 mM glutamine, and 10 U/ml each of penicillin and streptomycin. The cells were removed by centrifugation, and the culture supernatant was mixed slowly with ammonium sulfate until the solution was 50% saturated with the salt. The mixture was stirred overnight at 4° C., and the resultant protein precipitate was sedimented by centrifugation at 3,000 g for 30 min at 4° C. The protein pellet was resuspended in phosphate-buffered saline and dialyzed three times in 20 mM sodium phosphate, pH 7.0, at 4° C. The dialyzed antibody solution was loaded onto an FPLC Mono Q column, and the proteins were eluted by a gradient of NaCl from 0 to 1.0 M in 20 mM sodium phosphate, pH 7.0. The column fractions were assayed for antibody activity by ELISA. Purity of the antibody was analyzed by SDS-polyacrylamide gel electrophoresis. The size of the heavy chain of the monoclonal antibody (approximately 72 kd) corresponded to that of an IgM molecule. On Western blots, the 2F4 monoclonal antibody recognized specifically a 32-kd protein in a crude extract of bovine RPE microsomes.

The results show that labeled 32-kd protein was immunoprecipitated in a specific manner by the antibody-conjugated Affi-Gel resin. The immunoprecipitation of the protein was completely blocked when the antibody was incubated in the presence of 100 $\mu$M of carboxyl terminal peptide, but was not affected when the antibody was incubated with the same concentration of amino terminal bovine retinaldehyde binding protein. The immunoprecipitated protein co-migrated with retinaldehyde binding protein, as detected by Western immunoblot.

UV-visible Absorbance Spectrum of Retinaldehyde Binding Protein after Incubation with All-trans-retinal and Purification To maximize the recovery of photosensitive retinaldehyde binding protein, the RPE microsomes were first incubated in the dark with exogenous all-trans-retinal prior to solubilization and purification of retinaldehyde binding protein. Bovine retinaldehyde binding protein was purified from freshly isolated RPE cells under red or dim yellow light. Within 3 hours of enucleation, bovine eyes were hemisected to remove anterior structures, lens, vitreous, and neural retina. The RPE cells were removed by gently scraping the cell monolayer with a spatula, and preparations of microsomes were isolated by homogenization of the cells and centrifugation in cold 0.25 M sucrose buffer. The membranous protein was extracted in 1.2% digitonin solution at pH 6.5 and isolated efficiently by means of immunoaffinity chromatography as described below. The UV-visible absorbance spectra were determined using a Hitachi U-3000 recording spectrophotometer by scanning at wavelengths from 700 nm to 260 nm.

Figure 4A:
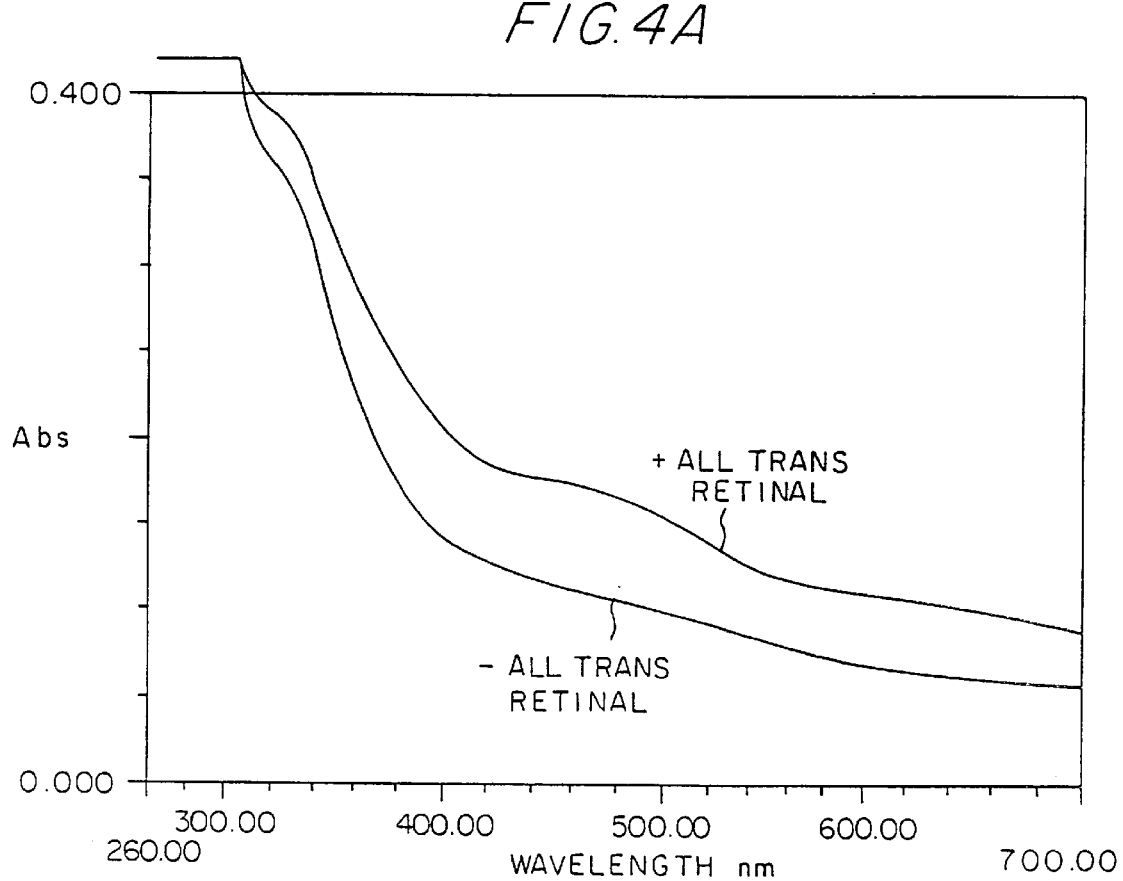
FIG. 4A shows the UV-visible absorbance spectrum of purified retinaldehyde binding protein bound to all-trans-retinal. The difference spectrum is shown in FIG. 4B.
Figure 4B:
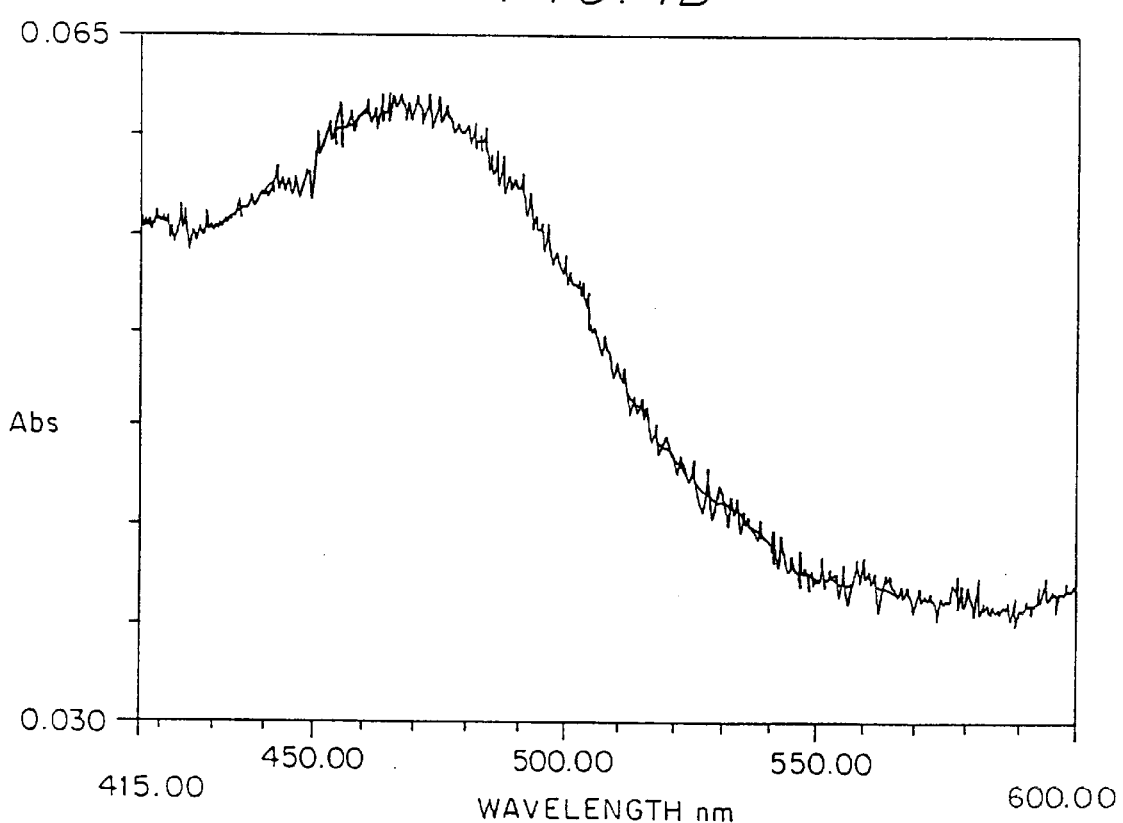

In FIG. 4A, the UV-visible absorbance spectrum of the purified retinaldehyde binding protein showed an absorbance in the visible region centered near wavelengths of 465 to 470 nm. This absorbance was not detected in purified retinaldehyde binding protein from RPE microsomes that had not been preincubated with exogenous all-trans-retinal. The results indicate that all-trans-retinal contributes necessarily to the difference spectrum seen in FIG. 4B where the broad difference spectrum resembles the absorbance spectrum of free all-trans-retinal ($\lambda_{max}$=389 nm), but it is shifted significantly to longer wavelengths.

Isolation of Retinaldehyde Binding Protein from Bovine RPE Cells by Immunoaffinity Chromatography RPE microsomes from 30 bovine eyes were prepared under dim yellow light. The membranes were incubated with 1.2% digitonin in 67 mM sodium phosphate buffer, pH 6.5, twice for 2 hours at 4° C. each time. The extracts were centrifuged in a Beckman TLS 55 rotor at 150,000 g for 15 min at 4° C. The supernatant (2.0 mg/ml, 1 ml) was diluted with 2 vols of binding buffer, containing 10 mM $Na_2HPO_4$, pH 7.2, and 0.5 M NaCl, and then incubated with 2F4-Affi-Gel resin 2 hrs at 4° C. with gentle agitation. The immunoaffinity gel was collected by centrifugation and washed in solution, containing 0.4% digitonin, 50 mM $Na_2HPO_4$, pH 7.0, and 0.33 M NaCl. To elute bound retinaldehyde binding protein, the gel was resuspended in buffer containing 100 $\mu$M carboxyl terminal, and the mixture was incubated for 2 hours at 4° C. with gentle agitation. The gel and eluate were separated using a small column, and the washing step was repeated once. The various steps of the immunoaffinity procedure were analyzed by SDS-polyacrylamide gel electrophoresis, followed by protein staining and immunoblot detection of retinaldehyde binding protein.

Bovine RPE extracts at different steps in the purification were run on protein gels visualized by silver staining and by Western immunoblot using bovine antibody against retinaldehyde binding protein. The purified protein consisted predominantly of a 32-kDa protein which reacted strongly to specific bovine antibodies against retinaldehyde binding protein. A few other proteins were found to co-purify along with retinaldehyde binding protein in a highly reproducible manner. It is possible that these other proteins form a multimeric complex or associate functionally with retinaldehyde binding protein. When the RPE microsomes were incubated with [$^3$H]-labeled retinals, only the 32-kDa protein covalently bound the radiolabeled isomers.

Isolation and Characterization of Human Retinaldehyde Binding Protein cDNA

Genomic and cDNA clones were identified by plaque hybridization to a radiolabeled RPE12 bovine retinaldehyde binding protein cDNA. NotI-digested $\lambda$FIXII DNA clones containing the human rgr gene were completely and partially cleaved with BamHI, EcoRI and SacI restriction enzymes. Restriction maps were determined by Southern blot hybridization of the resulting fragments using oligonucleotide probes complementary to the flanking T3 and T7 promoters. DNA sequencing was carried out using single and double strand phagemid DNA, sequence-specific primers, and Sequenase (U.S. Biochemical Corp., Cleveland, Ohio) or Bst DNA polymerase (Bio-Rad, Hercules, Calif.), according to the manufacturers' protocol.

RNA and DNA blot hybridizations were performed according to established techniques (Sambrook et al., Molecular Cloning: A Laboratory Manual, 1989). Human retina poly(A)$^+$RNA from 22 pooled tissue specimens (ages 16–70) was purchased from Clontech Laboratories, Inc. (Palo Alto, Calif.). Postmortem eyes were obtained from the Lions Doheny Eye Bank (Los Angeles, Calif.), and retina poly(A)$^+$RNAs from individuals were prepared using a Mini RiboSep Ultra mRNA Isolation Kit (Becton Dickinson Labware, Bedford, Mass.), according to instructions from the manufacturer.

Six human retinaldehyde binding protein cDNA clones were isolated from a $\lambda$gt10 retina library, following hybridization to the bovine retinaldehyde binding protein cDNA clone RPE12. One of these clones, HRGR1-2, contained a 1.3-kb incomplete cDNA insert and was used to determine the human retinaldehyde binding protein cDNA sequence from the nucleotide position 224 to the 3'-terminal poly(A)

tract (FIG. 5). The first 57 nucleotides of the actual 5'-end of the cDNA clone HRGR1-2 showed poor homology to the sequence of bovine retinaldehyde binding protein cDNA and appeared to be an artifact of cDNA cloning. This unknown sequence was later shown to be an inversion of the 5'-end of the human retinaldehyde binding protein cDNA.

The sequence of the cDNA from nucleotides 1 to 223 (FIG. 5) was determined by rapid amplification of the 5' end of human rgr mRNA with reagents from the 5'-Amplifinder RACE Kit (Clontech Laboratories, Inc.) using the RACE method according to Edwards et al., *Nucleic Acids Res.*, 19: 5227–5232, 1991. Ten pmoles of a human retinaldehyde binding protein-specific antisense primer, A290 (5'-ATGCGATGGCTGCACTGCTGC) (SEQ ID NO:5), were used in reverse transcription of 0.5 μg of pooled human retina poly(A)+RNA. Following the ligation of a single-stranded oligonucleotide anchor directly to the 3' end of the first-strand cDNAs, the 5'-end of the retinaldehyde binding protein cDNA was amplified using the A290 primer and an anchor primer (5'-CTGGTTCGGCCCACCTCT-GAAGGTTCCAGAATCGATAG) (SEQ ID NO:6) provided with the RACE Kit (Clontech Laboratories, Inc.) that was complementary to the anchor sequence. The amplification by PCR was carried out for 40 cycles, with each cycle performed for 1 min at 92° C., 1.5 min at 55° C., and 2 min at 72° C. The 5'-end PCR fragment was then subcloned and several clones were sequenced. The results of this primer extension and PCR was the amplification of a single major DNA fragment about 380 bp in length. The 5'-end cDNA fragment was then cloned, and several copies were sequenced. Multiple clones of the amplified 5'-end fragment ended with the adenosine at nucleotide position 1, thus this site may mark the major 5'-terminus of human retinaldehyde binding protein mRNA. About half (13/23) of the RACE clones contained a cytidine residue at nucleotide position 65 of the cDNA sequence, and the other half (10/23) contained thymidine. These results suggest that there is at least one common polymorphic difference in the human rgr gene at the DNA level. The alternative codons both encode threonine.

The complete nucleotide sequence of the human retinaldehyde binding protein cDNA (SEQ ID NO:3), derived from cDNA clone HRGR1-2 and the 5'-end PCR fragment, is 1414 nucleotides long, excluding the poly(A) tract (FIG. 5). The overlapping sequences between the cDNA clone HRGR1-2 and the amplified 5'-end cDNA fragment were identical. Translation of the human retinaldehyde binding protein cDNA from its 5'-most ATG codon to the in-phase stop codon yields an open reading frame of 291 amino acids (SEQ ID NO:4) with a cumulative molecular weight of 31,872. The 5'-untranslated region is 38 nucleotides long, and the putative translational initiation codon conforms to a consensus translational start site (Kozak, 1991). This initiation codon is preceded by an in-frame termination codon located 15 nucleotides upstream of the ATG sequence. A poly(A) tract of 12 adenosine residues was located at the 3' end of the cDNA clone.

Prior to amplification of the retinaldehyde binding protein cDNA 5' end by the RACE method, several other cDNA clones were characterized in an attempt to obtain a complete cDNA insert. One of these clones, HRGR33, contained a cDNA sequence that was in essence identical to that of the cDNA clone HRGR1-2, except that an insertion of 12 nucleotides was found after nucleotide position 274. This insertion did not terminate or shift the original open reading frame.

Comparison of Human and Bovine retinaldehyde Binding Protein

The deduced amino acid sequence of human retinaldehyde binding protein is 86% identical to that of bovine retinaldehyde binding protein and precisely aligns with the bovine amino acid sequence. The two proteins are 291 amino acids long and have homologous coterminal amino and carboxyl ends. The hydrophilic lysine[255] residue within the putative seventh transmembrane domain of retinaldehyde binding protein is conserved in both species and is expected to be the high-affinity binding site for retinal by analogy to homologous opsins. Other amino acid residues in retinaldehyde binding protein conform to conserved sequence motifs of G protein-coupled receptors as discussed for FIG. 5.

Rentinaldehyde binding protein differs from the vertebrate visual pigment in that a negatively charged residue, homologous to the glutamate[113] counterion in rhodopsin (Nathans, *Biochemistry*, 29: 9746–9752, 1990; Sakmar et al., *Proc. Natl. Acad. Sci. U.S.A.*, 86: 8309–8313, 1989; Zhukovsky & Oprian, *Science*, 246: 928–930, 1989), is not conserved as a counterion for potential protonated Schiff base in retinaldehyde binding protein. Instead, histidine[91] is found in the corresponding position of retinaldehyde binding protein, and the nearest acidic residue is aspartate[86] in human retinaldehyde binding protein and glutamate[86] in bovine retinaldehyde binding protein. The rhodopsin and retinochrome in squid also lack the conserved glutamate residue as a counterion near the amino-terminal portion of transmembrane helix III (Hara-Hishimura et al., *FEBS Lett.*, 271: 106–110, 1990; Hall et al., *Biochem. J.*, 274: 35–40, 1991). Retinaldehyde binding protein also has short amino- and carboxyl-terminal domains and a short connecting loop between transmembrane domains V and VI.

The divergent substitutions between human and bovine retinaldehyde binding protein are more numerous in the amino- and carboxyl-terminal domains and in the connecting loops between the putative transmembrane segments, particularly in the third connecting loop on the side of the carboxyl terminus. These regions of retinaldehyde binding protein are analogous with the third cytoplasmic loop and the carboxyl-terminal domain of other receptors and have been shown in the homologous receptors to interact with G proteins (Kobilka et al., *Science* 240:1310–1316, 1988; Konig et al., *Proc. Natl. Acad. Sci. USA* 86:6878–6882, 1989).

Structure of the Human rgr Gene

The structure of the human rgr gene was determined by restriction enzyme mapping, exon-intron mapping and nucleotide sequencing. Thirteen genomic clones with inserts of about 20 kb were isolated from a λFIXII library by probing with a human retinaldehyde binding protein cDNA. The complete gene was characterized by analysis of two overlapping genomic clones, λrgr12-1 and λrgr13-2. The λrgr12-1 clone contained the first four exons and 6.8 kb of the 5'-flanking region, but lacked the 3' end of the gene. The λrgr13-2 clone contained the entire gene.

Figure 6:
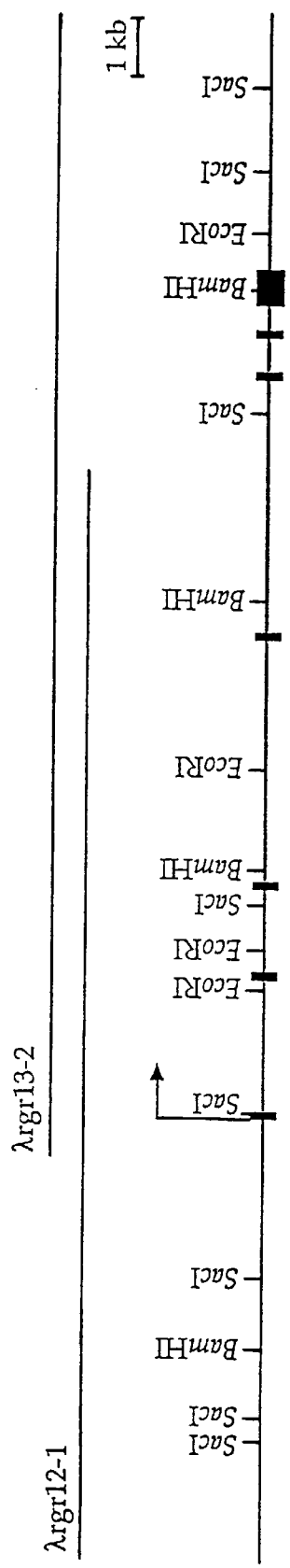
FIG. 6 shows the structure of the human rgr gene. The restriction map of the human rgr gene for BamH1, EcoR1, and SacI sites was determined from overlapping genomic DNA clones, λrgr12-1 and λrgr13-2. The transcriptional initiation site is marked by an arrow, and the exons are represented as solid boxes.

A restriction map of the human rgr gene was determined for BamHI, EcoRI and SacI cleavage sites (FIG. 6). The gene spans about 14.8 kb and is split into 7 exons, identified by nucleotide sequence (SEQ ID NO:19–25) (FIGS. 7A–7B). The transcriptional initiation site and the 5' end of exon 1 were inferred from the 5'-terminal cDNA sequence, as determined by the RACE method and the 5'-sequence upstream of the transcriptional initiation contains the promoter for the human rgr gene. Exon 7 encodes the carboxyl-terminal 43 amino acid residues of the protein and includes the contiguous 3'-untranslated cDNA sequence. The polyadenylation cleavage site was inferred from the cDNA clone HRGR1-2 and the site of its 3' poly(A) tract. The polyadenylation site was not preceded by a canonical recognition sequence, AATAAA, characteristic of mammalian poly(A) signals (Gilmartin and Nevins, Genes Dev. 3, 2180–2189, 1989).

The nucleotide sequence of the exons is identical to the cDNA sequence, except at two positions. The sequence at nucleotide position 979 of the cDNA contains guanosine; however, adenosine is found at this position in the genomic sequence (FIGS. 7A–7B). The codon specifying tyrosine$^{153}$ is TAT in the cDNA clone, but in the genomic clone the codon sequence is TAC. These sequence differences between the cDNA and gene clones may represent additional DNA polymorphisms in the human rgr gene. All of the intron-exon boundary sequences conform to consensus splice junctions by adherence to the GT/AG rule for intron termini.

Human rgr Gene Expression in Retina

In human retina, three major mRNAs, 1.5 kb, 2.4 kb, and 3.5 kb in length, and three larger faint transcripts were detected by hybridization to a cDNA fragment from clone HRGR1-2. The 1.5-kb and 3.5-kb major mRNAs are similar in size and relative intensity to the rgr mRNA transcripts in bovine RPE and retina. The results of the hybridization were similar whether the retinal RNA was from a group of donors and or from a single individual.

To investigate the possibility of multiple rgr genes, a human retinaldehyde binding protein cDNA probe was hybridized to human lung DNA cut with various restriction enzymes. The pattern of genomic fragments that hybridized with the cDNA probe was consistent with the restriction map. Only the approximate 2.8 kb BamHI fragment was not predicted from the map of the cloned gene. This difference may be due to a restriction fragment length polymorphism exhibited between the cloned rgr gene and the alleles from the isolated tissue.

Analysis of Human Retinaldehyde Binding Protein cDNA Clones

Figure 8:
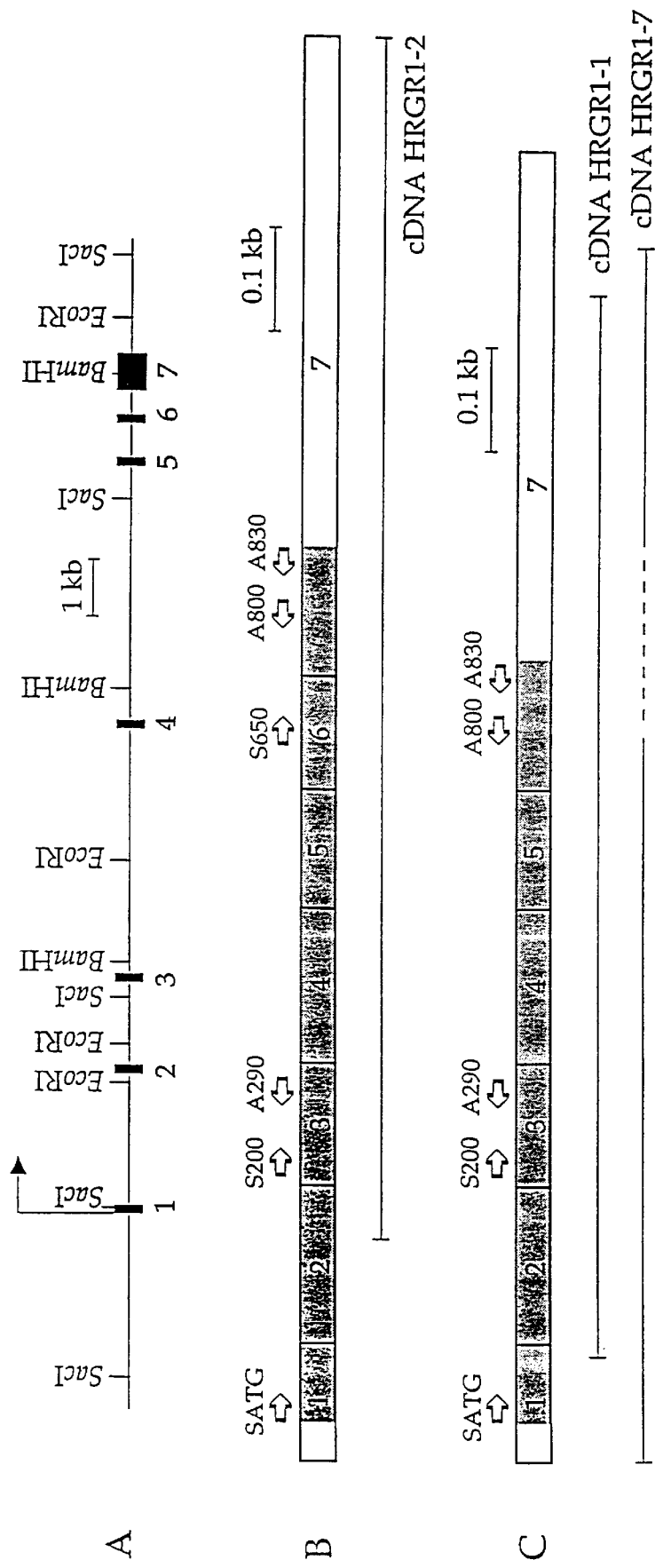
FIG. 8 shows the structural arrangement of the human rgr gene and isolated cDNA clones. Line A shows the structure and restriction map of the human rgr gene. The BamH1, EcoR1, and SacI cleavage sites were determined from overlapping genomic clones, λrgr12-1 and λrgr13-2. The seven exons of the gene are represented by the solid bars, and the transcriptional initiation site is shown by the arrow. Line B shows the human retinaldehyde binding protein cDNA and its relationship to the exons. The shaded area of the rectangle represents the protein-coding region, and the open areas represent the 5'- or 3'-untranslated regions. The location and orientation of oligonucleotide primers and probes that were used in this study are indicated by the open arrows. The partial cDNA clone, HRGR1-2, was sequenced on both strands and corresponds to the cDNA region that is depicted by the solid line. Line C shows human retinaldehyde binding protein cDNA clones containing the deletion of exon 6. The two cDNA clones, HRGR1-1 and HRGR1-7, were sequenced completely, except in the region depicted by the dashed lines. Both clones contained the identical deletion of 114 nucleotides.
Figure 9:
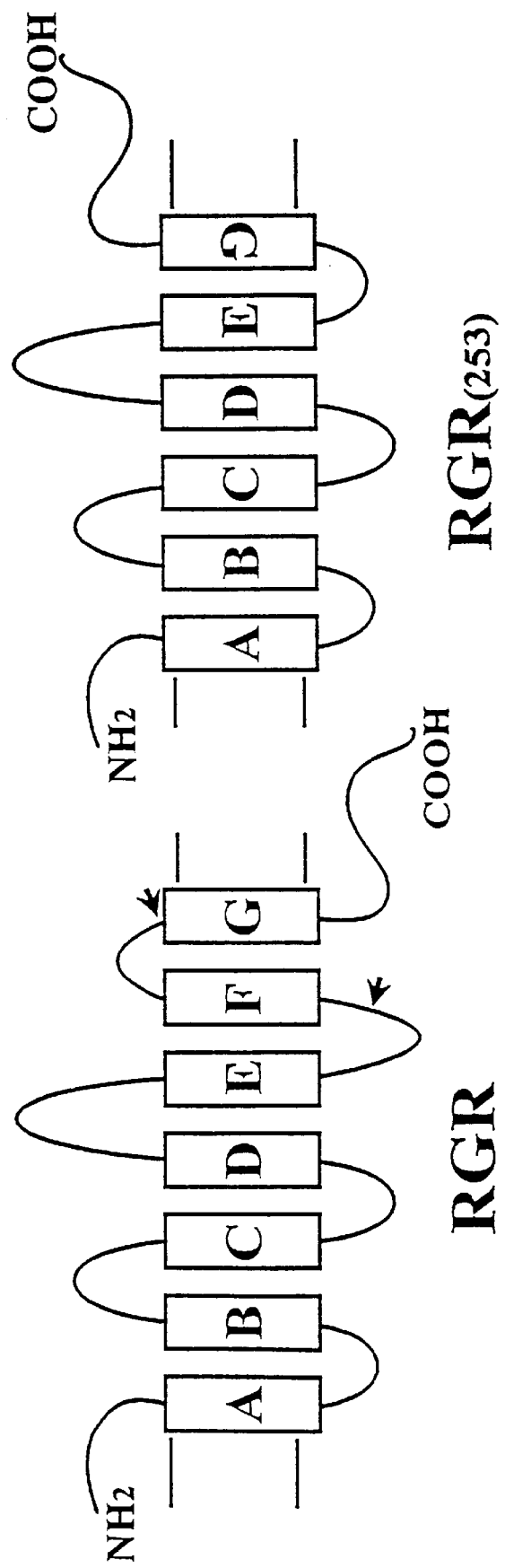
FIG. 9 shows a schematic representation of membrane-bound retinaldehyde binding protein (labeled "RGR") and the retinaldehyde binding $protein_{(253)}$ variant, (labeled "$RGR_{(253)}$"). Putative transmembrane domains that correspond to hydrophobic segments of human retinaldehyde binding protein are depicted by the rectangles A–G. The arrows mark the approximate position of the introns that flank exon 6, which is deleted in the retinaldehyde binding $protein_{(253)}$ variant.

The gene that encodes human retinaldehyde binding protein is made up of seven exons, each of which contains part of the protein-coding region (FIG. 8, line A). Exons 2, 3, 4, 5, 6 and 7 of the rgr gene encode the putative transmembrane domains B, C, D, E, F and G (FIG. 9), respectively. A major portion of the human retinaldehyde binding protein cDNA sequence was determined from the partial cDNA clone, HRGR1-2 (FIG. 8, line B), which was isolated from a λgt10 human retinal library.

In an effort to obtain a full-length cDNA, additional cDNA clones were isolated and characterized. Surprisingly, the cDNA sequences of two separate clones from the same cDNA library, clones HRGR1-1 and HRGR1-7 (FIG. 8, line C), were found to contain an identical deletion of 114 nucleotides. The deleted sequence corresponded precisely to the nucleotide sequence of exon 6 of the human rgr gene. The HRGR1-1 and HRGR1-7 cDNAs (SEQ ID NO:9) correspond to a shorter version of the retinaldehyde binding protein (SEQ ID NO:10) that has an in-frame deletion of 38 amino acid residues.

To determine the prevalence of cDNA clones with the 114-bp deletion, 20 different clones from the library were isolated and analyzed by amplification across the deletion region using a pair of PCR primers, SATG and A800 (see Table 3).

TABLE 3

Oligonucleotides Used as Primers or Probes

| Primer | Location of 5' End | Sequence | |
|---|---|---|---|
| Human | | | |
| SATG | 39 | ATGGCAGAGACCAGTGCCCTG | SEQ ID NO:11 |
| S200 | 282 | CCCTACGGCTCGGACGGCTGC | SEQ ID NO:12 |
| A290 | 369 | ATGCGATGGCTGCACTGCTGC | SEQ ID NO:5 |
| S650 | 722 | CATCCTGTATCTATACGCAGT | SEQ ID NO:13 |
| A800 | 857 | GCAGACCATCTCATTGCCCA | SEQ ID NO:14 |
| A830 | 911 | CTTGGTTCGGTCCTTCTCCCT | SEQ ID NO:15 |
| Bovine | | | |
| bvS300 | 426 | TGTCTTCTGCCTTCTGGG | SEQ ID NO:16 |
| bvA900 | 1115 | AACACAGGTCCGTGTGGC | SEQ ID NO:17 |

The location of the 5'-end nucleotide corresponds to the numbering of bovine and human retinaldehyde binding protein cDNA sequences. The orientation of oligonucleotides for the human sequence is shown in FIG. 8. With these primers, only clones that contain the translational start region will be amplified, and the cDNAs would be amplified across most of the protein-coding region. Following PCR, DNA fragments of two main sizes were detected. Five of the clones yielded a DNA fragment of ~830 bp, and four yielded a fragment of ~710 bp. The exact sizes of the PCR products expected for the intact and truncated cDNA were 819 and 705 bp, respectively. One of the cDNA clones that yielded the shorter PCR product was partially sequenced. The nucleotide sequence of the cDNA, HRGR6, confirmed that it too contained the 114-bp deletion that had been found previously in cDNA clones HRGR1-1 and HRGR1-7. Thus, the analysis of human retinaldehyde binding protein cDNA clones from a given retinal cDNA library suggests that about 44% of the clones contained a deletion of the nucleotide sequence of exon 6, while retaining the sequences from all other exons of the human rgr gene.

Analysis of Human Retinaldehyde Binding Protein mRNA

Human retina poly(A)$^+$RNA from 22 combined tissue specimens (ages 16–70) was purchased from Clontech Laboratories, Inc. (Palo Alto, Calif.). Postmortem eyes were obtained at random from the Lions Doheny Eye Bank (Los Angeles, Calif.), and retina poly(A)$^+$RNAs from individuals were prepared using a Mini RiboSep Ultra mRNA Isolation Kit (Becton Dickinson Labware, Bedford, Mass.), according to instructions from the manufacturer. The retinas were dissected and frozen in liquid nitrogen until processing.

Human or bovine retinaldehyde binding protein mRNA sequences were analyzed by amplification via reverse transcription and PCR (RT-PCR). The reverse transcriptase reaction was carried out with 10 pmoles of oligo(dT) or a human retinaldehyde binding protein-specific primer, A830 (Table 3), 0.5 to 1 µg of RNA, and 200 units of Superscript RNase H⁻ Reverse Transcriptase (GIBCO BRL Life Technologies, Inc., Gaithersburg, Md.). The reaction products were diluted 20-fold, and a region of the retinaldehyde binding protein cDNA was amplified using the primers in Table 3.

The cloning of numerous cDNAs that contain the deletion of a specific 114-bp nucleotide sequence indicates that corresponding mRNA transcripts may be present in human retina tissue. To ascertain independently the presence of transcripts with the deletion, designated the retinaldehyde binding protein-d transcript, the differentially spliced mRNA was assayed using reverse transcriptase and PCR (RT-PCR). The reverse transcriptase reaction was performed using the human retinaldehyde binding protein-specific A830 primer and poly(A)⁺RNA, either from the pooled retinas of 22 donors (ages 16 to 70) or from a single individual (age 84). A pair of PCR primers, S200 and A800 (Table 3), was used to amplify expected 576-bp and 462-bp fragments that correspond to the intact retinaldehyde binding protein and truncated retinaldehyde binding protein-d mRNAs, respectively.

The results of the RT-PCR assay indicated that DNA fragments of ~580 bp and ~470 bp were indeed amplified from both the individual and pooled human retina RNA. The relative amount of the ~470-bp PCR product was low, when derived from the pooled retina RNA, and about equal in abundance to the ~580-bp fragment, when amplified from the single-donor RNA. DNA blots of the PCR fragments were hybridized to radiolabeled oligonucleotide probes, A290 and S650 (Table 3). The A290 probe corresponds to a sequence found in both types of transcripts, and the S650 probe corresponds to a sequence located within the deleted region. The A290 probe hybridized to both the ~580-bp and ~470-bp DNA fragments, while the S650 probe hybridized to the ~580-bp band only. No PCR bands were detected in the controls. The ~470-bp PCR fragment, that was derived from the single donor, was subcloned, sequenced and found to contain the 114-bp deletion.

Retina mRNAs from eight other donors (ages 52 to 98) were also analyzed individually by RT-PCR. The retinaldehyde binding protein-d transcript was detected in every sample and, in most cases, was only slightly less abundant than the intact retinaldehyde binding protein mRNA. No bands were amplified in the controls in which reverse transcriptase was omitted in the procedure. Variation in the amount of retinaldehyde binding protein-d transcript by age, race or sex was not detected in these experiments.

Expression of Retinaldehyde Binding Protein$_{(253)}$ in Human Retina

The sequence of the retinaldehyde binding protein-d mRNA predicts a 253-amino-acid protein (retinaldehyde binding protein$_{(253)}$) with a calculated molecular weight of 27,726. The expression of the predicted retinaldehyde binding protein$_{(253)}$ in the retina was investigated by immunoblot assay using an antipeptide antibody (hcDE⅞) directed against the carboxyl terminal amino acid sequence of human retinaldehyde binding protein. A synthetic peptide that corresponds to the carboxyl terminal amino acid sequence (amino acid residues 279–291 of SEQ ID NO:4) of human retinaldehyde binding protein was obtained from the Division of Biology, Caltech (Pasadena, Calif.). The peptide was synthesized using an automated peptide synthesizer and then conjugated to keyhole limpet hemocyanin (KLH). The production of rabbit antipeptide antisera was carried out by Cocalico Biologicals, Reamstown, Pa. The anti-human retinaldehyde binding protein antibody was affinity-purified by immunoadsorption to the synthetic peptide, coupled to CNBr-activated Sepharose (Pharmacia LKB Biotechnology, Piscataway, N.J.). The retinal extracts were prepared from part of the same donor tissues that were used for the RNA isolation. In each sample, the antibody bound strongly to a 32-kDa protein, the size of which agrees with the calculated molecular weight of the intact human retinaldehyde binding protein. In addition, a band that corresponds to a protein of about 28 kDa was detected in the retinas of two individuals. The signal for the 28-kDa band varied between the two positive samples and was either equal or lower in intensity to that of the 32-kDa protein band.

Analysis of Bovine Retinaldehyde Binding Protein mRNA

To determine if a similar retinaldehyde binding protein-d mRNA transcript is expressed in the eyes of another species, RT-PCR analysis of total RNA from bovine retina and poly(A)⁺RNA from RPE was carried out using oligo(dT) as the cDNA primer, and bvS300 and bvA900 (Table 3) as PCR primers. The PCR primers flank the homologous 114-bp deletion sequence in the bovine retinaldehyde binding protein mRNA, and the expected PCR products are 690-bp and 576-bp DNA fragments that correspond to bovine retinaldehyde binding protein and a putative retinaldehyde binding protein-d mRNA, respectively. The results showed that only a single band, ~680 bp in length, was amplified from both retina and RPE RNA. No band that corresponded to a 576-bp DNA fragment was detected by the RT-PCR assay. On a Southern blot, the ~680-bp PCR product was the only band detected by hybridization to a bovine retinaldehyde binding protein cDNA probe.

The predicted retinaldehyde binding protein$_{(253)}$ protein lacks the transmembrane domain F. Thus, transmembrane domain G in retinaldehyde binding protein$_{(253)}$ may be expected to traverse the membrane in reverse orientation (FIG. 9) or become part of an extended cytoplasmic carboxyl domain. It is unlikely, then, that retinaldehyde binding protein$_{(253)}$ would be able to bind retinal properly, if at all. The retinaldehyde binding protein-d mRNA and retinaldehyde binding protein$_{(253)}$ are not found in bovine retina or RPE, so these products are obviously not essential for vision. If synthesis of high levels of retinaldehyde binding protein$_{(253)}$ were indeed to occur in human retina, the variant protein may actually perturb functions of retinal Müller cells or the RPE.

Production of an Antibody for Specific Binding to the Human Retinaldehyde Binding Protein$_{(253)}$ A peptide that corresponds to a unique amino acid sequence in the human protein, referred to as retinaldehyde binding protein$_{(253)}$, was synthesized by means of an automated peptide synthesizer and contained the sequence of amino acids, GlyLysSerGlyHisLeuGlnVal-ProAlaLeuIleAlaLys (SEQ ID NO:18), in the amino to carboxyl terminal direction. A cysteine (Cys) residue was added to the carboxyl terminus of the peptide, and a multiple antigen peptide (MAP) system was used to synthesize multiple copies of the peptide on a polylysine core. The molecular weight of the MAP-peptide is increased to greater than 10,000, thus eliminating the conjugation step required for immunization. The MAP-peptide was synthesized by an automated peptide synthesizer. Antipeptide antisera were generated by immunizing rabbits with the MAP-peptide mixed with an equal volume of complete Freund's adjuvant. The rabbits were boosted 14 and 21 days later with 50 μg of the immunogen mixed with an equal volume of incomplete Freund's adjuvant. Immunoreactivity of the antisera was tested by enzyme-linked immunosorbent assay (ELISA). The antibody was affinity-purified by binding to the cognate synthetic peptide coupled to CNBr-activated Sepharose column.

Immunoblot Analysis of Human Retinaldehyde Binding Protein$_{(253)}$

The retinas from postmortem human eyes were excised and stored in liquid nitrogen until processing. The retinas were homogenized in buffer containing 67 mM sodium phosphate, pH 6.7, 250 mM sucrose, and 0.2 mM phenylmethylsulfonyl fluoride. The homogenates were centrifuged at 500 g for 10 min to remove unbroken cells and cell debris, and the membranes were collected from the low-speed supernatant by centrifugation at 150,000 g for 20 minutes at 4° C. The membrane pellet was resuspended in 67 mM sodium phosphate, pH 6.7, and 250 mM sucrose buffer, and 20 μg of protein per sample were electrophoresed in a 12% polyacrylamide-0.1% SDS gel. The protein concentrations were determined by the Bio-Rad Protein Assay (Bio-Rad Laboratories, Hercules, Calif.). After electrophoresis, the proteins were transferred to nitrocellulose membranes for immunoblot analysis. The blot was blocked 1 hour with 1% gelatin in Tris-buffer saline and incubated with affinity-purified anti-human retinaldehyde binding protein or retinaldehyde binding protein$_{(253)}$ antibody and then with anti-rabbit IgG that had been conjugated to alkaline phosphatase (Togo, Inc., Burlingame, Calif.). The detection of the bound antibodies was accomplished using nitro blue tetrazolium (NBT) and 5-bromo 4-chloro 3-indolyl phosphate (BCIP) as the chromogen substrates.

Retinas of seven individuals (A–G) were analyzed by Western immunoblot for presence of the retinaldehyde binding protein$_{(253)}$ using an antibody, RGR-DE9, which is directed against the unique amino acid sequence of retinaldehyde binding protein$_{(253)}$ GlyLysSerGlyHisLeuGlnVal-ProAlaLeuIleAlaLys (SEQ ID NO:18). The RGR-DE9 antibody has the ability to bind preferentially to retinaldehyde binding protein$_{(253)}$ over human retinaldehyde binding protein. The 28-kDa retinaldehyde binding protein$_{(253)}$ was present in the retinas of some of the donors (individual D and F), and absent in others. Moreover, the amount of retinaldehyde binding protein$_{(253)}$ in positive individuals varied appreciably, being 10-fold higher in individual D than F. Thus far, only 3 of 15 eye donors, aged 52 to 98 years, had detectable levels of retinaldehyde binding protein$_{(253)}$ in the retina. All had the 32-kDa retinaldehyde binding protein which was detected by the hcDE⅞ antibody. The hcDE⅞ antibody also recognized retinaldehyde binding protein$_{(253)}$. In individual D, the amount of retinaldehyde binding protein$_{(253)}$ was even greater than that of the 32-kDa retinaldehyde binding protein.

Isolation and Recombinant Expression of Human Retinaldehyde Binding Protein and Retinaldehyde Binding Protein$_{(253)}$ Isolation of human retinaldehyde binding protein can be prepared from human RPE microsomes according to the immunoaffinity chromatography method described for isolating bovine retinaldehyde binding protein. Antibodies to the human retinaldehyde binding protein carboxyl terminus (hcDE⅞) and antibodies specific to retinaldehyde binding protein$_{(253)}$ can be used in the immunoaffinity chromatography column to affinity purify the human retinaldehyde binding protein and retinaldehyde binding protein$_{(253)}$, respectively.

Expression of human retinaldehyde binding protein and retinaldehyde binding protein$_{(253)}$ in a recombinant system may be desirable for the production of ample quantities of retinaldehyde binding protein. Along this line, there may be used baculoviral vectors such as pVL941, pVL1393, pVL1392, and pBlueBac, which are commercially available pUC-based vectors conferring ampicillin resistance and containing the polyhedrin gene promoter and baculovirus sequences flanking the site(s) for insertion of the gene of interest. The baculovirus flanking sequences facilitate homologous recombination between the vector and the wild-type baculoviral DNA. In all the above-mentioned baculoviral vectors, the gene of interest is cloned downstream of the polyhedrin promoter. A cDNA clone encoding human retinaldehyde binding protein and retinaldehyde binding protein$_{(253)}$ can be cloned into a baculoviral vector by standard techniques of molecular biology (Sambrook et al., Molecular Cloning: A Laboratory Manual, Second edition, Cold Spring Harbor Laboratory, Cold Spring Harbor, N.Y., 1989; Ausubel et al., Current Protocols in Molecular Biology, Wiley Interscience, NY, 1987–1994). Recombinant baculoviral clones can be screened and then expressed and cultured in *Spodoptera frugiperda* (Sf9) cells according to Ausubel et al. Parker et al., J. Biol. Chem. 266:519–527, 1991, demonstrated with turkey β-adrenergic receptor the general utility of the baculovirus system for production of large quantities of native G protein-coupled receptors. WO 92/05244 discloses the expression of G protein coupled receptors in yeast. The entire contents of the above references are incorporated herein by reference.

It will be appreciated that the DNA sequence and encoded retinaldehyde binding protein of the invention provides the basis for a variety of different uses. For instance, it is well recognized in the art that oligonucleotide probes/primers (sense and anti-sense RNA and DNA) can be synthesized which are diagnostic for human retinaldehyde binding protein mRNA and the rgr gene. Probes/primers specific for hum an retinaldehyde binding protein and retinaldehyde binding protein-d (encoding retinaldehyde binding protein$_{(253)}$) mRNA can be readily synthesized. By being able to measure the levels of retinaldehyde binding protein-d mRNA, assays that test for drugs and chemicals that affect the levels of retinaldehyde binding protein-d mRNA or retinaldehyde binding protein$_{(253)}$ protein can be developed. In addition, the DNA can be used as genetic markers, for PCR primers, for forensic identification and for tissue typing.

The assay for retinaldehyde binding protein-d mRNA and/or the retinaldehyde binding protein$_{(253)}$ can be conducted on surgically excised choroidal neovascular membranes for diagnostic purposes or tissue-typing. Submacular choroidal neovascular membranes are removed in a newly developed surgical procedure to improve the central vision of patients with age-related macular degeneration (Amin et al., Investigative Ophthalmol. Visual Sci. 35:3178, 1994). Similarly, the various retinaldehyde binding proteins or peptide fragments (e.g. the peptide of SEQ ID NO:18) thereof can be used to raise antibodies specific for a retinaldehyde binding protein, which could then be used in a diagnostic assay for binding and measurement of retinaldehyde binding protein and retinaldehyde binding protein$_{(253)}$. Non-limiting examples of these specific antibodies are discussed above.

The expression of retinaldehyde binding protein$_{(253)}$, and the level of retinaldehyde binding protein-d mRNA from which it is translated, is absent or present at various levels in individual retinas. Determination of the level present in the retina would be indicative of retinal disease. Purified retinaldehyde binding protein or retinaldehyde binding protein$_{(253)}$ can be immobilized on a Western blot or ELISA plate and then incubated with serum samples. Human antibodies complexed with retinaldehyde binding protein on the blot can then be detected with rabbit anti-human IgG. Uveitis, an inflammatory autoimmune disease, is a condition in which anti-retinaldehyde binding protein antibodies may be present in a patient's blood. As discussed previously, the presence of the altered retinaldehyde binding protein may be associated with retinal disease or propensity to retinal disease. Thus, determination of the presence of the altered retinaldehyde binding protein can serve as a diagnosis of said disease or propensity.

Transplantation of RPE is considered as a treatment for macular degeneration. The assay of retinaldehyde binding protein gene products can be used to type or assess the normality of donor RPE cells.

Furthermore, certain forms of retinal disease may well be treated through the use of anti-sense oligonucleotide therapy where the approach is to halt DNA transcription or messenger RNA translation with triple helix-forming anti-sense RNA or oligonucleotides. Anti-sense RNA complementary to the sense RNA is a powerful way of regulating the biological functions of RNA molecules. Through the formation of a stable duplex between sense RNA and anti-sense RNA or a triple helix, the sense RNA-transcript can be rendered inactive and untranslatable in an individual who is autosomal dominant for retinal disease caused by the presence of inherited altered or abnormal retinaldehyde binding protein. The invention allows for using anti-sense and triple helix-forming oligonucleotides for evaluation of anti-sense oligonucleotide therapy regimens.

It will also be appreciated that the retinaldehyde binding protein is useful in receptor binding assays to identify agonists and antagonists.

Further uses for the present invention include using (1) isolated retinaldehyde-bound retinaldehyde binding protein as a biosensor for absorption of light in the visible range of wavelengths and, (2) light absorbance of retinaldehyde binding protein bound to all-trans-retinal as a pH indicator due to retinaldehyde binding protein's light absorbance at wavelengths near 466 nm being decreased as the pH is raised towards pH 8, or increased as the pH is lower towards pH 3.

Due to the formation of a covalent bond between the Lys$^{255}$ residue of retinaldehyde binding protein and all-trans-retinal, via a Schiff base, the light absorbance property of the retinaldehyde binding protein—all-trans-retinal conjugate in the visible wavelengths can be used as a pH indicator. Light absorbance at 466 nm is increased by lowering the pH, which favors the protonated form of the conjugate, whereas raising the pH to 8.0 abolishes the $\lambda_{max}$ peak at 466 nm. In contrast, concomitant inverse changes in extinction are observed for a peak at ~366–370 nm. The absorbance curves at various pH all cross at an isosbestic point. The effect of pH on interconversion is reversible in the dark. This system provides a method of measuring pH through the level of light absorbance at ~466 nm and would be extremely useful, particularly in situations where conventional pH measurement is difficult, such as would be encountered in applications involving microvolume samples.

The retinaldehyde binding proteins of the present invention can also be used to separate the retinaldehydes, all-trans-retinal and 11-cis-retinal, from a crude mixture or extract for purification purposes. Many uses for purified all-trans-retinal or 11-cis-retinal are known. U.S. Pat. No. 5,183,817 discloses that all-trans-retinal or 11-cis-retinal in combination with a minoxidil compound is synergistically effective in stimulating or increasing the rate at which hair grows on mammalian skin. These retinaldehydes can also be used in combination with veterinary preparations and feeds to increase the rate of growth of fur in fur-bearing animals and to retard moulting. The all-trans-retinal can also be converted to vitamin A by application of known methods as disclosed in U.S. Pat. No. 3,227,763. In AU 9348175, a latent energy storage device for the conversion and storage of solar energy is disclosed which uses the photosensitive stereoisomer configuration of 11-cis-retinal to convert by photoisomerization into a second stable stereoisomer configuration with release of energy. This second stereoisomer configuration is reconverted back to the photosensitive stereoisomer configuration by the solar energy absorbing stereoselective regeneration agent, all-trans-retinal.

Retinaldehyde binding protein, solubilized with an appropriate surface active agent (to provide a pseudo-membrane environment without causing denaturation of the retinaldehyde binding protein), such as digitonin or dodecyl maltoside, can be bound to an affinity chromatography column to effect separation and purification of 11-cis-retinal and all-trans-retinal from a crude mixture (e.g. homogenate). After 11-cis-retinal and all-trans-retinal are passed through the column and is bound to retinaldehyde binding protein, the column is washed, and the retinaldehydes, 11-cis-retinal and all-trans-retinal can then be eluted from the column with hydroxylamine as a reducing agent. Hydroxylamine reverses the binding of 11-cis-retinal or all-trans-retinal to the lysine residue at position 255 of the bovine and human retinaldehyde binding protein.

Of course, proteins, in general, can be used as molecular weight markers for reference in the separation or purification of proteins by electrophoresis or chromatography. Hydrolyzed protein is commonly used as a growth media component for culturing microorganisms.

The foregoing description of the specific embodiments will so fully reveal the general nature of the invention that others can, by applying knowledge within the skill of the art (including the contents of the references cited herein), readily modify and/or adapt for various applications such as specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology of the present specification is to be interpreted by skilled artisan in light of the teachings and guidance presented herein, in combination with the knowledge of one of ordinary skill in the art.

What is claimed is:

1. An isolated nucleic acid molecule, comprising a nucleotide sequence encoding a protein having an amino acid sequence of SEQ ID NO:10.

2. An isolated nucleic acid molecule comprising a nucleotide sequence of SEQ ID NO:9.

3. An isolated nucleic acid molecule, comprising a nucleotide sequence encoding a peptide of SEQ ID NO:18 or fragments thereof capable of being bound by a molecule which includes an antigen binding portion of an antibody specific for the peptide of SEQ ID NO:18.

4. An expression vector containing the isolated nucleic acid molecule of claim 1.

5. A host cell transformed with the expression vector of claim 4.

6. An isolated nucleic acid molecule, comprising a nucleotide sequence selected from the group consisting of SEQ ID NO:19, SEQ ID NO:20, SEQ ID NO:21, SEQ ID NO:22, SEQ ID NO:23, SEQ ID NO:24, SEQ ID NO:25, and SEQ ID NO:3.

7. An isolated nucleic acid molecule in accordance with claim 6, which consists of a nucleotide sequence selected from the group consisting of SEQ ID NO:19, SEQ ID NO:20, SEQ ID NO:21, SEQ ID NO:22, SEQ ID NO:23, SEQ ID NO:24, SEQ ID NO:25, and SEQ ID NO:3.

8. An expression vector containing the isolated nucleic acid molecule of claim 6.

9. A host cell transformed with the expression vector of claim 8.

10. An isolated nucleic acid molecule, comprising a nucleotide sequence encoding a protein having an amino acid sequence selected from the group consisting of SEQ ID NO:4 and SEQ ID NO:2.

11. The isolated nucleic acid molecule in accordance with claim 10, wherein said nucleotide sequence encoding the protein is selected from the group consisting of SEQ ID NO:3 and SEQ ID NO:1.

12. An expression vector containing the isolated nucleic acid molecule of claim 10.

13. A host cell transformed with the expression vector of claim 12.

14. The isolated nucleic acid molecule in accordance with claim 3, wherein said nucleotide sequence encodes a peptide of SEQ ID NO:18.

15. An expression vector containing the isolated nucleic acid molecule of claim 2.

16. A host cell transformed with the expression vector of claim 15.

* * * * *

SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
      (A) LENGTH: 1420 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 17..889

(xi) SEQUENCE DESCRIPTION: SEQ ID NO:1:

```
GAGAAAGGCA GAGAGA ATG GCA GAG TCT GGG ACC CTG CCC ACT GGC TTC          49
               Met Ala Glu Ser Gly Thr Leu Pro Thr Gly Phe
                 1               5                  10

GGG GAG CTG GAG GTG CTG GCC GTG GGG ACG GTG CTG CTG GTG GAA GCT        97
Gly Glu Leu Glu Val Leu Ala Val Gly Thr Val Leu Leu Val Glu Ala
             15                  20                  25

CTT TCT GGT CTC AGC CTA AAC ATC CTG ACC ATC CTC TCT TTC TGC AAG       145
Leu Ser Gly Leu Ser Leu Asn Ile Leu Thr Ile Leu Ser Phe Cys Lys
         30                  35                  40

ACC CCA GAG CTG CGG ACC CCC AGC CAC CTG CTG GTG TTG AGC TTG GCG       193
Thr Pro Glu Leu Arg Thr Pro Ser His Leu Leu Val Leu Ser Leu Ala
     45                  50                  55

CTG GCC GAC AGT GGA ATC AGC CTG AAC GCC CTC GTT GCA GCC ACG TCC       241
Leu Ala Asp Ser Gly Ile Ser Leu Asn Ala Leu Val Ala Ala Thr Ser
 60                  65                  70                  75

AGC CTC CTC CGG CGC TGG CCC TAC GGC TCG GAA GGC TGC CAG GCT CAC       289
Ser Leu Leu Arg Arg Trp Pro Tyr Gly Ser Glu Gly Cys Gln Ala His
                 80                  85                  90

GGC TTC CAG GGC TTT GTC ACG GCA CTG GCC AGC ATC TGC AGC AGC GCA       337
Gly Phe Gln Gly Phe Val Thr Ala Leu Ala Ser Ile Cys Ser Ser Ala
             95                 100                 105

GCC GTC GCC TGG GGG CGC TAT CAC CAC TTC TGC ACC CGC AGC CGA CTG       385
Ala Val Ala Trp Gly Arg Tyr His His Phe Cys Thr Arg Ser Arg Leu
        110                 115                 120

GAT TGG AAC ACG GCC GTC TCC CTG GTG TTC TTC GTA TGG CTG TCT TCT       433
Asp Trp Asn Thr Ala Val Ser Leu Val Phe Phe Val Trp Leu Ser Ser
    125                 130                 135

GCC TTC TGG GCA GCA CTG CCC CTC CTG GGC TGG GGC CAC TAT GAC TAT       481
Ala Phe Trp Ala Ala Leu Pro Leu Leu Gly Trp Gly His Tyr Asp Tyr
140                 145                 150                 155

GAG CCG CTG GGG ACC TGC TGC ACT CTG GAC TAT TCC AGG GGG GAC AGA       529
Glu Pro Leu Gly Thr Cys Cys Thr Leu Asp Tyr Ser Arg Gly Asp Arg
                160                 165                 170

AAC TTC ACC AGC TTC CTT TTC ACC ATG GCC TTT TTC AAC TTC CTC CTG       577
Asn Phe Thr Ser Phe Leu Phe Thr Met Ala Phe Phe Asn Phe Leu Leu
            175                 180                 185

CCC CTC TTC ATC ACA GTC GTG TCC TAT CGG CTC ATG GAG CAG AAA CTC       625
Pro Leu Phe Ile Thr Val Val Ser Tyr Arg Leu Met Glu Gln Lys Leu
        190                 195                 200

GGG AAG ACC AGC CGT CCC CCG GTG AAC ACC GTC CTG CCA GCC AGG ACG       673
Gly Lys Thr Ser Arg Pro Pro Val Asn Thr Val Leu Pro Ala Arg Thr
    205                 210                 215
```

-continued

```
CTG CTG CTC GGC TGG GGC CCC TAC GCT CTC CTG TAT CTG TAT GCC ACC        721
Leu Leu Leu Gly Trp Gly Pro Tyr Ala Leu Leu Tyr Leu Tyr Ala Thr
220                 225                 230                 235

ATC GCG GAT GCA ACC TCC ATC TCC CCC AAG CTG CAG ATG GTG CCC GCT        769
Ile Ala Asp Ala Thr Ser Ile Ser Pro Lys Leu Gln Met Val Pro Ala
                240                 245                 250

CTC ATT GCC AAG GCA GTA CCC ACA GTC AAC GCC ATG AAC TAT GCC CTG        817
Leu Ile Ala Lys Ala Val Pro Thr Val Asn Ala Met Asn Tyr Ala Leu
            255                 260                 265

GGC AGC GAG ATG GTG CAC AGG GGA ATC TGG CAA TGC CTC TCG CCA CAG        865
Gly Ser Glu Met Val His Arg Gly Ile Trp Gln Cys Leu Ser Pro Gln
        270                 275                 280

AGG AGA GAG CAC AGC CGA GAG CAG TGAGCCTCTC TGGGGGGCTT CCCAGACCCA       919
Arg Arg Glu His Ser Arg Glu Gln
    285                 290

GGCCCACCCT GGCCTTCCTG GACTGAGCCC CTGCCTGGGG AATCCTGTCC AGCAGCCTCA      979

GGAGCCAAGC TCCAAACACT CACCCTTCAT CCCCGATGGC CCTTTGAGCC TGGTCCAAGG     1039

CTGGACACAG GGGATTCAGA GAAAAACCAG ACTACATGGA ATGAGCCCGG ACTCTGGAGC     1099

CACACGGACC TGTGTTGGCC ATAGCTCTCC ACATAGAGGC TGAGAGACCT TGGAAAAGTC     1159

ACACTCTCTG ACTCTGCTTC CTGGCCCCTA ACGTAAGGAT GTTAATACGG ACTTTGGGTC     1219

TGTAGTGAAG CTTGAACTTG GTAGCATATA TTCATATACA CATAGAAGCT GCTGCTCATT     1279

AGTACAGCTC TTAGGATTCA GAGACCTACA TAGAAAGGGT GAGAGCCCCA GGTCTGGTTG     1339

TGGGAGCTCA GCCCAGGCTG CCAGTGTTCA AACACCTCTT ATTAAATCGT GATCTCGTAC     1399

AGGTGACTTC CAAAAAAAAA A                                               1420
```

(2) INFORMATION FOR SEQ ID NO:2:

(i) SEQUENCE CHARACTERISTICS:
       (A) LENGTH: 291 amino acids
       (B) TYPE: amino acid
       (D) TOPOLOGY: linear (ii) MOLECULE TYPE: protein (xi) SEQUENCE DESCRIPTION: SEQ ID NO:2:

```
Met Ala Glu Ser Gly Thr Leu Pro Thr Gly Phe Gly Glu Leu Glu Val
1               5                   10                  15

Leu Ala Val Gly Thr Val Leu Val Glu Ala Leu Ser Gly Leu Ser
            20                  25                  30

Leu Asn Ile Leu Thr Ile Leu Ser Phe Cys Lys Thr Pro Glu Leu Arg
        35                  40                  45

Thr Pro Ser His Leu Leu Val Leu Ser Leu Ala Leu Ala Asp Ser Gly
    50                  55                  60

Ile Ser Leu Asn Ala Leu Val Ala Ala Thr Ser Ser Leu Leu Arg Arg
65                  70                  75                  80

Trp Pro Tyr Gly Ser Glu Gly Cys Gln Ala His Gly Phe Gln Gly Phe
                85                  90                  95

Val Thr Ala Leu Ala Ser Ile Cys Ser Ser Ala Val Ala Trp Gly
            100                 105                 110

Arg Tyr His His Phe Cys Thr Arg Ser Arg Leu Asp Trp Asn Thr Ala
        115                 120                 125

Val Ser Leu Val Phe Phe Val Trp Leu Ser Ser Ala Phe Trp Ala Ala
    130                 135                 140

Leu Pro Leu Leu Gly Trp Gly His Tyr Asp Tyr Glu Pro Leu Gly Thr
145                 150                 155                 160
```

```
Cys Cys Thr Leu Asp Tyr Ser Arg Gly Asp Arg Asn Phe Thr Ser Phe
            165                 170                 175

Leu Phe Thr Met Ala Phe Phe Asn Phe Leu Leu Pro Leu Phe Ile Thr
            180                 185                 190

Val Val Ser Tyr Arg Leu Met Glu Gln Lys Leu Gly Lys Thr Ser Arg
            195                 200                 205

Pro Pro Val Asn Thr Val Leu Pro Ala Arg Thr Leu Leu Leu Gly Trp
            210                 215                 220

Gly Pro Tyr Ala Leu Leu Tyr Leu Tyr Ala Thr Ile Ala Asp Ala Thr
225                 230                 235                 240

Ser Ile Ser Pro Lys Leu Gln Met Val Pro Ala Leu Ile Ala Lys Ala
            245                 250                 255

Val Pro Thr Val Asn Ala Met Asn Tyr Ala Leu Gly Ser Glu Met Val
            260                 265                 270

His Arg Gly Ile Trp Gln Cys Leu Ser Pro Gln Arg Arg Glu His Ser
            275                 280                 285

Arg Glu Gln
290
```

(2) INFORMATION FOR SEQ ID NO:3:

(i) SEQUENCE CHARACTERISTICS:
        (A) LENGTH: 1426 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 39..911

(xi) SEQUENCE DESCRIPTION: SEQ ID NO:3:

```
AGAGACAGCT GGGCCACTGG CAGTGAGGGA GAGTGAGG ATG GCA GAG ACC AGT           53
                                         Met Ala Glu Thr Ser
                                           1               5

GCC CTG CCC ACT GGC TTC GGG GAG CTC GAG GTG CTG GCT GTG GGG ATG        101
Ala Leu Pro Thr Gly Phe Gly Glu Leu Glu Val Leu Ala Val Gly Met
             10                  15                  20

GTG CTA CTG GTG GAA GCT CTC TCC GGT CTC AGC CTC AAT ACC CTG ACC        149
Val Leu Leu Val Glu Ala Leu Ser Gly Leu Ser Leu Asn Thr Leu Thr
         25                  30                  35

ATC TTC TCT TTC TGC AAG ACC CCG GAG CTG CGG ACT CCC TGC CAC CTA        197
Ile Phe Ser Phe Cys Lys Thr Pro Glu Leu Arg Thr Pro Cys His Leu
             40                  45                  50

CTG GTG CTG AGC TTG GCT CTT GCG GAC AGT GGG ATC AGC CTG AAT GCC        245
Leu Val Leu Ser Leu Ala Leu Ala Asp Ser Gly Ile Ser Leu Asn Ala
         55                  60                  65

CTC GTT GCA GCC ACA TCC AGC CTT CTC CGG CGC TGG CCC TAC GGC TCG        293
Leu Val Ala Ala Thr Ser Ser Leu Leu Arg Arg Trp Pro Tyr Gly Ser
 70                  75                  80                  85

GAC GGC TGC CAG GCT CAC GGC TTC CAG GGC TTT GTG ACA GCG TTG GCC        341
Asp Gly Cys Gln Ala His Gly Phe Gln Gly Phe Val Thr Ala Leu Ala
                 90                  95                 100

AGC ATC TGC AGC AGT GCA GCC ATC GCA TGG GGG CGT TAT CAC CAC TAC        389
Ser Ile Cys Ser Ser Ala Ala Ile Ala Trp Gly Arg Tyr His His Tyr
            105                 110                 115

TGC ACC CGT AGC CAG CTG GCC TGG AAC TCA GCC GTC TCT CTG GTG CTC        437
Cys Thr Arg Ser Gln Leu Ala Trp Asn Ser Ala Val Ser Leu Val Leu
            120                 125                 130
```

| | | |
|---|---|---|
| TTC GTG TGG CTG TCT TCT GCC TTC TGG GCA GCT CTG CCC CTT CTG GGT<br>Phe Val Trp Leu Ser Ser Ala Phe Trp Ala Ala Leu Pro Leu Leu Gly<br>135                        140                        145 | | 485 |
| TGG GGT CAC TAT GAC TAT GAG CCA CTG GGG ACA TGC TGC ACC CTG GAC<br>Trp Gly His Tyr Asp Tyr Glu Pro Leu Gly Thr Cys Cys Thr Leu Asp<br>150                       155                   160                     165 | | 533 |
| TAC TCC AAG GGG GAC AGA AAC TTC ACC AGC TTC CTC TTC ACC ATG TCC<br>Tyr Ser Lys Gly Asp Arg Asn Phe Thr Ser Phe Leu Phe Thr Met Ser<br>               170                       175                     180 | | 581 |
| TTC TTC AAC TTC GCC ATG CCC CTC TTC ATC ACG ATC ACT TCC TAC AGT<br>Phe Phe Asn Phe Ala Met Pro Leu Phe Ile Thr Ile Thr Ser Tyr Ser<br>               185                       190                     195 | | 629 |
| CTC ATG GAG CAG AAA CTG GGG AAG AGT GGC CAT CTC CAG GTA AAC ACC<br>Leu Met Glu Gln Lys Leu Gly Lys Ser Gly His Leu Gln Val Asn Thr<br>               200                       205                     210 | | 677 |
| ACT CTG CCA GCA AGG ACG CTG CTC CTC GGC TGG GGC CCC TAT GCC ATC<br>Thr Leu Pro Ala Arg Thr Leu Leu Leu Gly Trp Gly Pro Tyr Ala Ile<br>215                       220                     225 | | 725 |
| CTG TAT CTA TAC GCA GTC ATC GCA GAC GTG ACT TCC ATC TCC CCC AAA<br>Leu Tyr Leu Tyr Ala Val Ile Ala Asp Val Thr Ser Ile Ser Pro Lys<br>230                       235                   240                   245 | | 773 |
| CTG CAG ATG GTG CCC GCC CTC ATT GCC AAA ATG GTG CCC ACG ATC AAT<br>Leu Gln Met Val Pro Ala Leu Ile Ala Lys Met Val Pro Thr Ile Asn<br>               250                       255                     260 | | 821 |
| GCC ATC AAC TAT GCC CTG GGC AAT GAG ATG GTC TGC AGG GGA ATC TGG<br>Ala Ile Asn Tyr Ala Leu Gly Asn Glu Met Val Cys Arg Gly Ile Trp<br>               265                       270                     275 | | 869 |
| CAG TGC CTC TCA CCG CAG AAG AGG GAG AAG GAC CGA ACC AAG<br>Gln Cys Leu Ser Pro Gln Lys Arg Glu Lys Asp Arg Thr Lys<br>280                       285                     290 | | 911 |
| TGAGCCTGCC ACCCTGGAGT GAGCCCCAGG CCAGGAGGCT GTTCCAGGAG TCCTGCCCAG | | 971 |
| CAGCCTCGGT GGCCAAGCCC AGACACTCAC CCACCTTCCC CAGTGGCCCC GTGGATCCTG | | 1031 |
| GTCCTAGGCT GGACACAGGA TTCAGAAAGA CACCAGGCTG CACAGAAAGA GCCAGATGGA | | 1091 |
| CCTGAGTGTC GGTCACAGCC CCCTACACTC AAGGCTGAGA GGCCTCAGGA AAGTCATTCC | | 1151 |
| TTTTTAAAAA TAATAATAAA TGTAAGGGGG TACAGTGCAG TTTTGTTACA TGGATAGATT | | 1211 |
| GCCTAGTGGT GAAGTCTGGG CTTTTAGTGT AACCATCACC CTAATAATAT ACGTTGTACC | | 1271 |
| CATTAAGTTA TTTCTCATCC CTCACCCCCT CCCACCTTGT CACCCTTCTG AGTCTCCAAT | | 1331 |
| GTCTATTATT CCACACTCCA TGTCCACGTG TACACATTAT TTAGCTCCCA CTTACAAGTG | | 1391 |
| AGAACATGTG GTATTTGACT TCAAAAAAA AAAA | | 1426 |

(2) INFORMATION FOR SEQ ID NO:4:

(i) SEQUENCE CHARACTERISTICS:
        (A) LENGTH: 291 amino acids
        (B) TYPE: amino acid
        (D) TOPOLOGY: linear (ii) MOLECULE TYPE: protein (xi) SEQUENCE DESCRIPTION: SEQ ID NO:4:

Met Ala Glu Thr Ser Ala Leu Pro Thr Gly Phe Gly Glu Leu Glu Val
1               5                   10                    15

Leu Ala Val Gly Met Val Leu Val Glu Ala Leu Ser Gly Leu Ser
              20                     25                     30

Leu Asn Thr Leu Thr Ile Phe Ser Phe Cys Lys Thr Pro Glu Leu Arg
              35                     40                     45

Thr Pro Cys His Leu Leu Val Leu Ser Leu Ala Leu Ala Asp Ser Gly

```
            50                  55                  60
Ile Ser Leu Asn Ala Leu Val Ala Ala Thr Ser Ser Leu Leu Arg Arg
 65                  70                  75                  80

Trp Pro Tyr Gly Ser Asp Gly Cys Gln Ala His Gly Phe Gln Gly Phe
                 85                  90                  95

Val Thr Ala Leu Ala Ser Ile Cys Ser Ser Ala Ala Ile Ala Trp Gly
                100                 105                 110

Arg Tyr His His Tyr Cys Thr Arg Ser Gln Leu Ala Trp Asn Ser Ala
            115                 120                 125

Val Ser Leu Val Leu Phe Val Trp Leu Ser Ser Ala Phe Trp Ala Ala
        130                 135                 140

Leu Pro Leu Leu Gly Trp Gly His Tyr Asp Tyr Glu Pro Leu Gly Thr
145                 150                 155                 160

Cys Cys Thr Leu Asp Tyr Ser Lys Gly Asp Arg Asn Phe Thr Ser Phe
                165                 170                 175

Leu Phe Thr Met Ser Phe Phe Asn Phe Ala Met Pro Leu Phe Ile Thr
                180                 185                 190

Ile Thr Ser Tyr Ser Leu Met Glu Gln Lys Leu Gly Lys Ser Gly His
            195                 200                 205

Leu Gln Val Asn Thr Thr Leu Pro Ala Arg Thr Leu Leu Leu Gly Trp
        210                 215                 220

Gly Pro Tyr Ala Ile Leu Tyr Leu Tyr Ala Val Ile Ala Asp Val Thr
225                 230                 235                 240

Ser Ile Ser Pro Lys Leu Gln Met Val Pro Ala Leu Ile Ala Lys Met
                245                 250                 255

Val Pro Thr Ile Asn Ala Ile Asn Tyr Ala Leu Gly Asn Glu Met Val
                260                 265                 270

Cys Arg Gly Ile Trp Gln Cys Leu Ser Pro Gln Lys Arg Glu Lys Asp
            275                 280                 285

Arg Thr Lys
    290

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:5:

ATGCGATGGC TGCACTGCTG C                                           21

(2) INFORMATION FOR SEQ ID NO:6:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:6:

CTGGTTCGGC CCACCTCTGA AGGTTCCAGA ATCGATAG                          38

(2) INFORMATION FOR SEQ ID NO:7:
```

(i) SEQUENCE CHARACTERISTICS:
 (A) LENGTH: 12 base pairs
 (B) TYPE: nucleic acid
 (C) STRANDEDNESS: single
 (D) TOPOLOGY: linear (ii) MOLECULE TYPE: cDNA (xi) SEQUENCE DESCRIPTION: SEQ ID NO:7:

TGTCTCCCAC AG                                                                12

(2) INFORMATION FOR SEQ ID NO:8:

(i) SEQUENCE CHARACTERISTICS:
  (A) LENGTH: 4 amino acids
  (B) TYPE: amino acid
  (C) STRANDEDNESS: single
  (D) TOPOLOGY: linear (ii) MOLECULE TYPE: peptide (xi) SEQUENCE DESCRIPTION: SEQ ID NO:8:

Val Ser His Arg
1

(2) INFORMATION FOR SEQ ID NO:9:

(i) SEQUENCE CHARACTERISTICS:
  (A) LENGTH: 1201 base pairs
  (B) TYPE: nucleic acid
  (C) STRANDEDNESS: single
  (D) TOPOLOGY: linear (ii) MOLECULE TYPE: cDNA (ix) FEATURE:
  (A) NAME/KEY: CDS
  (B) LOCATION: 39..797

(xi) SEQUENCE DESCRIPTION: SEQ ID NO:9:

```
AGAGACAGCT GGGCCACTGG CAGTGAGGGA GAGTGAGG ATG GCA GAG ACC AGT          53
                                        Met Ala Glu Thr Ser
                                          1               5

GCC CTG CCC ACT GGC TTC GGG GAG CTC GAG GTG CTG GCT GTG GGG ATG       101
Ala Leu Pro Thr Gly Phe Gly Glu Leu Glu Val Leu Ala Val Gly Met
         10                  15                  20

GTG CTA CTG GTG GAA GCT CTC TCC GGT CTC AGC CTC AAT ACC CTG ACC       149
Val Leu Leu Val Glu Ala Leu Ser Gly Leu Ser Leu Asn Thr Leu Thr
             25                  30                  35

ATC TTC TCT TTC TGC AAG ACC CCG GAG CTG CGG ACT CCC TGC CAC CTA       197
Ile Phe Ser Phe Cys Lys Thr Pro Glu Leu Arg Thr Pro Cys His Leu
         40                  45                  50

CTG GTG CTG AGC TTG GCT CTT GCG GAC AGT GGG ATC AGC CTG AAT GCC       245
Leu Val Leu Ser Leu Ala Leu Ala Asp Ser Gly Ile Ser Leu Asn Ala
     55                  60                  65

CTC GTT GCA GCC ACA TCC AGC CTT CTC CGG CGC TGG CCC TAC GGC TCG       293
Leu Val Ala Ala Thr Ser Ser Leu Leu Arg Arg Trp Pro Tyr Gly Ser
 70                  75                  80                  85

GAC GGC TGC CAG GCT CAC GGC TTC CAG GGC TTT GTG ACA GCG TTG GCC       341
Asp Gly Cys Gln Ala His Gly Phe Gln Gly Phe Val Thr Ala Leu Ala
             90                  95                 100

AGC ATC TGC AGC AGT GCA GCC ATC GCA TGG GGG CGT TAT CAC CAC TAC       389
Ser Ile Cys Ser Ser Ala Ala Ile Ala Trp Gly Arg Tyr His His Tyr
        105                 110                 115

TGC ACC CGT AGC CAG CTG GCC TGG AAC TCA GCC GTC TCT CTG GTG CTC       437
Cys Thr Arg Ser Gln Leu Ala Trp Asn Ser Ala Val Ser Leu Val Leu
    120                 125                 130
```

```
TTC GTG TGG CTG TCT TCT GCC TTC TGG GCA GCT CTG CCC CTT CTG GGT      485
Phe Val Trp Leu Ser Ser Ala Phe Trp Ala Ala Leu Pro Leu Leu Gly
        135                 140                 145

TGG GGT CAC TAT GAC TAT GAG CCA CTG GGG ACA TGC TGC ACC CTG GAC      533
Trp Gly His Tyr Asp Tyr Glu Pro Leu Gly Thr Cys Cys Thr Leu Asp
150                 155                 160                 165

TAC TCC AAG GGG GAC AGA AAC TTC ACC AGC TTC CTC TTC ACC ATG TCC      581
Tyr Ser Lys Gly Asp Arg Asn Phe Thr Ser Phe Leu Phe Thr Met Ser
                170                 175                 180

TTC TTC AAC TTC GCC ATG CCC CTC TTC ATC ACG ATC ACT TCC TAC AGT      629
Phe Phe Asn Phe Ala Met Pro Leu Phe Ile Thr Ile Thr Ser Tyr Ser
            185                 190                 195

CTC ATG GAG CAG AAA CTG GGG AAG AGT GGC CAT CTC CAG GTG CCC GCC      677
Leu Met Glu Gln Lys Leu Gly Lys Ser Gly His Leu Gln Val Pro Ala
        200                 205                 210

CTC ATT GCC AAA ATG GTG CCC ACG ATC AAT GCC ATC AAC TAT GCC CTG      725
Leu Ile Ala Lys Met Val Pro Thr Ile Asn Ala Ile Asn Tyr Ala Leu
215                 220                 225

GGC AAT GAG ATG GTC TGC AGG GGA ATC TGG CAG TGC CTC TCA CCG CAG      773
Gly Asn Glu Met Val Cys Arg Gly Ile Trp Gln Cys Leu Ser Pro Gln
230                 235                 240                 245

AAG AGG GAG AAG GAC CGA ACC AAG TGAGCCTGCC ACCCTGGAGT GAGCCCCAGG     827
Lys Arg Glu Lys Asp Arg Thr Lys
                250

CCAGGAGGCT GTTCCAGGAG TCCTGCCCAG CAGCCTCGGT GGCCAAGCCC AGACACTCAC    887

CCACCTTCCC CAGTGGCCCC GTGGATCCTG GTCCTAGGCT GGACACAGGA TTCAGAAAGA    947

CACCAGGCTG CACAGAAAGA GCCAGATGGA CCTGAGTGTC GGTCACAGCC CCCTACACTC   1007

AAGGCTGAGA GGCCTCAGGA AAGTCATTCC TTTTTAAAAA TAATAATAAA TGTAAGGGGG   1067

TACAGTGCAG TTTTGTTACA TGGATAGATT GCCTAGTGGT GAAGTCTGGG CTTTTAGTGT   1127

AACCATCACC CTAATAATAT ACGTTGTACC CATTAAGTTA TTTCTCATCC CTCACCCCCT   1187

CCCACCTTGT CACC                                                    1201

(2) INFORMATION FOR SEQ ID NO:10:

(i) SEQUENCE CHARACTERISTICS:
        (A) LENGTH: 253 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:10:

Met Ala Glu Thr Ser Ala Leu Pro Thr Gly Phe Gly Glu Leu Glu Val
1               5                   10                  15

Leu Ala Val Gly Met Val Leu Leu Val Glu Ala Leu Ser Gly Leu Ser
            20                  25                  30

Leu Asn Thr Leu Thr Ile Phe Ser Phe Cys Lys Thr Pro Glu Leu Arg
        35                  40                  45

Thr Pro Cys His Leu Leu Val Leu Ser Leu Ala Leu Ala Asp Ser Gly
    50                  55                  60

Ile Ser Leu Asn Ala Leu Val Ala Ala Thr Ser Ser Leu Leu Arg Arg
65                  70                  75                  80

Trp Pro Tyr Gly Ser Asp Gly Cys Gln Ala His Gly Phe Gln Gly Phe
                85                  90                  95

Val Thr Ala Leu Ala Ser Ile Cys Ser Ser Ala Ala Ile Ala Trp Gly
            100                 105                 110
```

```
Arg Tyr His His Tyr Cys Thr Arg Ser Gln Leu Ala Trp Asn Ser Ala
        115                 120                 125

Val Ser Leu Val Leu Phe Val Trp Leu Ser Ser Ala Phe Trp Ala Ala
130                 135                 140

Leu Pro Leu Leu Gly Trp Gly His Tyr Asp Tyr Glu Pro Leu Gly Thr
145             150                 155                 160

Cys Cys Thr Leu Asp Tyr Ser Lys Gly Asp Arg Asn Phe Thr Ser Phe
                165                 170                 175

Leu Phe Thr Met Ser Phe Phe Asn Phe Ala Met Pro Leu Phe Ile Thr
            180                 185                 190

Ile Thr Ser Tyr Ser Leu Met Glu Gln Lys Leu Gly Lys Ser Gly His
            195                 200                 205

Leu Gln Val Pro Ala Leu Ile Ala Lys Met Val Pro Thr Ile Asn Ala
        210                 215                 220

Ile Asn Tyr Ala Leu Gly Asn Glu Met Val Cys Arg Gly Ile Trp Gln
225                 230                 235                 240

Cys Leu Ser Pro Gln Lys Arg Glu Lys Asp Arg Thr Lys
                245                 250

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:11:

ATGGCAGAGA CCAGTGCCCT G                                              21

(2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:12:

CCCTACGGCT CGGACGGCTG C                                              21

(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:13:

CATCCTGTAT CTATACGCAG T                                              21

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
```

-continued (D) TOPOLOGY: linear (ii) MOLECULE TYPE: oligonucleotide (xi) SEQUENCE DESCRIPTION: SEQ ID NO:14:

GCAGACCATC TCATTGCCCA                                               20

(2) INFORMATION FOR SEQ ID NO:15:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO:15:

CTTGGTTCGG TCCTTCTCCC T                                             21

(2) INFORMATION FOR SEQ ID NO:16:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO:16:

TGTCTTCTGC CTTCTGGG                                                 18

(2) INFORMATION FOR SEQ ID NO:17:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: oligonucleotide (xi) SEQUENCE DESCRIPTION: SEQ ID NO:17:

AACACAGGTC CGTGTGGC                                                 18

(2) INFORMATION FOR SEQ ID NO:18:

(i) SEQUENCE CHARACTERISTICS:
            (A) LENGTH: 14 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:18:

Gly Lys Ser Gly His Leu Gln Val Pro Ala Leu Ile Ala Lys
1               5                   10

(2) INFORMATION FOR SEQ ID NO:19:

(i) SEQUENCE CHARACTERISTICS:
            (A) LENGTH: 776 base pairs
            (B) TYPE: nucleic acid
            (C) STRANDEDNESS: single
            (D) TOPOLOGY: linear (ii) MOLECULE TYPE: DNA (genomic)

```
       (ix) FEATURE:
             (D) OTHER INFORMATION: /note= Exon 1 corresponds to
                    nucleotides 323...439

(xi) SEQUENCE DESCRIPTION: SEQ ID NO:19:

AGCTGCGGCT CAAATCCCTC CTCCTGCTCC CCTCCCCTGG TTATGCAACT CTTTTCCAAT      60

TAGGCTCTCA GCCACACACC ATTTGGATTC CCCGACCTTA ATCCTGTGCA ATGGGGCTGA     120

AATGAATGAG ACAGGGCTCC ATTCTGGCTT CACAAAGGCT GCATTGTCCA ACTCGTGAAT     180

GGGTTCCTTC TGCTTGGGCC AAGAGGACCA TTTGCAGCGG GGAGGCATCC AGAAACAGCC     240

CAAGGTCCAA CATAATAACC TGCATGTGCC TCCACGCACA TGGGATGGCC CTTTAAAAGG     300

GAGGGCCTGG CTGTGGGAAG CCAGAGACAG CTGGGCCACT GGCAGTGAGG GAGAGTGAGG     360

ATGGCAGAGA CCAGTGCCCT GCCCACTGGC TTCGGGGAGC TCGAGGTGCT GGCTGTGGGG     420

ATGGTGCTAC TGGTGGAAGG TGAGCCAGGC AGAACCTGGG GTGCAGCGGG GGCCCAGTGG     480

GTTCTGAGGA CCCAGGCCAC CAGTGTGGAG CTGGCAAGGA GAGGAGAGGT CCCCAAACCC     540

AGCTGGGTGT CCGGTCCCAT TGGCTGCCTT CCCCTCTGTG CCCGGACTCG GGGTGTTCT     600

GACAATTGAA CCTGTGAGGT GCAGCACACT GCCCGCTGGG AGCAGAGAGG AAGCCAGGCA     660

AGGGTCAGGG AGGGAGGGAC TTTGAAAGGG GACATCTGCC CAGGAGATGA TCAAGAGCCA     720

GGCTTTAGGA CTTTTCATGT CCCTCCAGCC GGGAGAAAAT TTAATCCACT CCTTGG        776

(2) INFORMATION FOR SEQ ID NO:20:

(i) SEQUENCE CHARACTERISTICS:
             (A) LENGTH: 329 base pairs
             (B) TYPE: nucleic acid
             (C) STRANDEDNESS: single
             (D) TOPOLOGY: linear (ii) MOLECULE TYPE: DNA (genomic)

(ix) FEATURE:
             (D) OTHER INFORMATION: /note= Exon 2 corresponds to
                    nucleotides 59...215

(xi) SEQUENCE DESCRIPTION: SEQ ID NO:20:

GTTCTGACCC CAGCTGGGCC TCAGCAGCCC CAATGCCAGC CCCCACCCTT CCTTTCAGCT      60

CTCTCCGGTC TCAGCCTCAA TACCCTGACC ATCTTCTCTT TCTGCAAGAC CCCGGAGCTG     120

CGGACTCCCT GCCACCTACT GGTGCTGAGC TTGGCTCTTG CGGACAGTGG GATCAGCCTG     180

AATGCCCTCG TTGCAGCCAC ATCCAGCCTT CTCCGGTACC AGCCCCCTCC CCAGTCCACA     240

GGCTCTGGGG TCCTGCCTGG GGCCTGACCC CTGGGCCCTG GGCAGCCAGG CCAAGGGCAT     300

TTTTACTACT TACAGAAAAT TGGCCAAGG                                      329

(2) INFORMATION FOR SEQ ID NO:21:

(i) SEQUENCE CHARACTERISTICS:
             (A) LENGTH: 311 base pairs
             (B) TYPE: nucleic acid
             (C) STRANDEDNESS: single
             (D) TOPOLOGY: linear (ii) MOLECULE TYPE: DNA (genomic)

(ix) FEATURE:
             (D) OTHER INFORMATION: /note= Exon 3 corresponds to
                    nucleotides 34...155

(xi) SEQUENCE DESCRIPTION: SEQ ID NO:21:

GGAGAGGTCA CTGGTGCCCA GTGTCTCCCA CAGGCGCTGG CCCTACGGCT CGGACGGCTG      60
```

```
CCAGGCTCAC GGCTTCCAGG GCTTTGTGAC AGCGTTGGCC AGCATCTGCA GCAGTGCAGC      120

CATCGCATGG GGGCGTTATC ACCACTACTG CACCCGTATG TATCTGGGCT CCTGGAGTGG      180

AGGGACACCG ATGCAGTGTG GAGAGGATAA GAGGCAGGGA GGGGCAGTCA TAACTAGCTA      240

CTGCTCCGTG TTTCCCAGTA CAGGGAAGTG TGGGTAGGTG TGAGTGTGCA TGCATAGGCA      300

CTCATTTCAG G                                                          311
```

(2) INFORMATION FOR SEQ ID NO:22:

(i) SEQUENCE CHARACTERISTICS:
        (A) LENGTH: 334 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (D) OTHER INFORMATION: /note= Exon 4 corresponds to
            nucleotides 102...255

(xi) SEQUENCE DESCRIPTION: SEQ ID NO:22:

```
CACTTGAAGG ACACTCTTC  GAGATCAGGA AGTCCATTCT TTCTCACTCT ATCAGGCCAT       60

CTCCTCCTCA CAACCTCCTC TTCTTCCTCT GTCCTGTGCA GGTAGCCAGC TGGCCTGGAA      120

CTCAGCCGTC TCTCTGGTGC TCTTCGTGTG GCTGTCTTCT GCCTTCTGGG CAGCTCTGCC      180

CCTTCTGGGT TGGGGTCACT ACGACTATGA GCCACTGGGG ACATGCTGCA CCCTGGACTA      240

CTCCAAGGGG GACAGGTGAG GTGGGAGGAG CAGCTTCGAG GCTCCTATCC ATGGGAATCT      300

TGGCTTTGAA CTCCTATGAC AAGGGTGCCC CAGC                                 334
```

(2) INFORMATION FOR SEQ ID NO:23:

(i) SEQUENCE CHARACTERISTICS:
        (A) LENGTH: 304 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (D) OTHER INFORMATION: /note= Exon 5 corresponds to
            nucleotides 68...185

(xi) SEQUENCE DESCRIPTION: SEQ ID NO:23:

```
TGGGTCCTTG AGGGCAGCTG GCCATCCCTG AGAGCTAACC CCAATCCTCC ACCCGCTCTC       60

CCTGTAGAAA CTTCACCAGC TTCCTCTTCA CCATGTCCTT CTTCAACTTC GCCATGCCCC      120

TCTTCATCAC GATCACTTCC TACAGTCTCA TGGAGCAGAA ACTGGGGAAG AGTGGCCATC      180

TCCAGGTAAG GACCCCCTTC CGGAGTGTTA TCTGATGGTG CAGCGCAGCT CCAGGCTCTT      240

GGTGTCCCGA ACAAAGAATT GGATGTGACA CACACAAACA GCAAAACAAA TATTCATTGC      300

TTTT                                                                  304
```

(2) INFORMATION FOR SEQ ID NO:24:

(i) SEQUENCE CHARACTERISTICS:
        (A) LENGTH: 417 base pairs
        (B) TYPE: nucleic acid
        (C) STRANDEDNESS: single
        (D) TOPOLOGY: linear (ii) MOLECULE TYPE: DNA (genomic)

(ix) FEATURE:

(D) OTHER INFORMATION: /note= Exon 6 corresponds to
                    nucleotides 195...308

(xi) SEQUENCE DESCRIPTION: SEQ ID NO:24:

AAAAGGCTTA AGGTCACACA GTCTTAAACA ACAGAGAGGC CCATCTGGTC CCAAGTTCCC      60

CTGCAGACTC AGCCCCCTCC TGAAGCCTGG TCCATGCTGC CCGCCCTGCT GAGTGCTGAC     120

CTGGTTTTCT TGGCCACATA GGGCTGTGGG CCACCTGGAG CAAGCTGACA TCTCCTGTGA     180

CAATTTCTCC CCAGGTAAAC ACCACTCTGC CAGCAAGGAC GCTGCTGCTC GGCTGGGGCC     240

CCTATGCCAT CCTGTATCTA TACGCAGTCA TCGCAGACGT GACTTCCATC TCCCCCAAAC     300

TGCAGATGGT ACAGATACTT CTAGTACCTA AAACTAGACC CCTCTCCATC TTTGTTCTCT     360

GTCTCATCTC ATCTCACTTT CTGGATTTAT GACCTCTGTG TCAGTCTCTT CCTTTCT       417

(2) INFORMATION FOR SEQ ID NO:25:

(i) SEQUENCE CHARACTERISTICS:
            (A) LENGTH: 694 base pairs
            (B) TYPE: nucleic acid
            (C) STRANDEDNESS: single
            (D) TOPOLOGY: linear (ii) MOLECULE TYPE: DNA (genomic)

(ix) FEATURE:
            (D) OTHER INFORMATION: /note= Exon 7 corresponds to
                nucleotides 39...670

(xi) SEQUENCE DESCRIPTION: SEQ ID NO:25:

CTTTGAAGCT TCTTTTCTGG ACTTTTCTGC CACAACAGGT GCCCGCCCTC ATTGCCAAAA      60

TGGTGCCCAC GATCAATGCC ATCAACTATG CCCTGGGCAA TGAGATGGTC TGCAGGGGAA     120

TCTGGCAGTG CCTCTCACCG CAGAAGAGGG AGAAGGACCG AACCAAGTGA GCCTGCCACC     180

CTGGAGTGAG CCCCAGGCCA GGAGGCTGTT CCAGGAGTCC TGCCCAGCAG CCTCAGTGGC     240

CAAGCCCAGA CACTCACCCA CCTTCCCCAG TGGCCCCGTG GATCCTGGTC CTAGGCTGGA     300

CACAGGATTC AGAAAGACAC CAGGCTGCAC AGAAAGAGCC AGATGGACCT GAGTGTCGGT     360

CACAGCCCCC TACACTCAAG GCTGAGAGGC CTCAGGAAAG TCATTCCTTT TTAAAAATAA     420

TAATAAATGT AAGGGGGTAC AGTGCAGTTT TGTTACATGG ATAGATTGCC TAGTGGTGAA     480

GTCTGGGCTT TTAGTGTAAC CATCACCCTA ATAATATACG TTGTACCCAT TAAGTTATTT     540

CTCATCCCTC ACCCCCTCCC ACCTTGTCAC CCTTCTGAGT CTCCAATGTC TATTATTCCA     600

CACTCCATGT CCACGTGTAC ACATTATTTA GCTCCCACTT ACAAGTGAGA ACATGTGGTA     660

TTTGACTTTC TGTTTTTGAG TTATTTCACT TAAA                                694